(12) United States Patent
Gangadharan et al.

(10) Patent No.: US 12,130,293 B2
(45) Date of Patent: *Oct. 29, 2024

(54) CLINICAL DIAGNOSIS OF NON-ALCOHOLIC FATTY LIVER DISEASE USING A PANEL OF HUMAN BLOOD PROTEIN BIOMARKERS

(71) Applicant: ShOx Science Limited, Hong Kong (CN)

(72) Inventors: Bevin Gangadharan, Oxfordshire (GB); Abhinav Kumar, Reading (GB); Raymond A. Dwek, Oxfordshire (GB); Nicole Zitzmann, Oxfordshire (GB); Mark Thursz, Berkhamstead (GB); Jeremy Francis Lars Cobbold, Witney (GB)

(73) Assignee: SHOX SCIENCE LIMITED, Kowloon (HK)

( * ) Notice: Subject to any disclaimer, the term of this patent is extended or adjusted under 35 U.S.C. 154(b) by 0 days.

This patent is subject to a terminal disclaimer.

(21) Appl. No.: 17/746,341

(22) Filed: May 17, 2022

(65) Prior Publication Data

US 2023/0117596 A1 Apr. 20, 2023

Related U.S. Application Data

(63) Continuation of application No. 16/326,737, filed as application No. PCT/GB2017/052486 on Aug. 23, 2017, now Pat. No. 11,366,124.

(30) Foreign Application Priority Data

Aug. 24, 2016 (GB) .................................. 1614455

(51) Int. Cl.
G01N 33/68 (2006.01)

(52) U.S. Cl.
CPC ... *G01N 33/6893* (2013.01); *G01N 2333/775* (2013.01); *G01N 2333/811* (2013.01); *G01N 2800/085* (2013.01); *G01N 2800/56* (2013.01)

(58) Field of Classification Search
CPC ....... G01N 2333/775; G01N 2333/811; G01N 2800/085; G01N 2800/56
See application file for complete search history.

(56) References Cited

U.S. PATENT DOCUMENTS

| | | |
|---|---|---|
| 2005/0064516 A1* | 3/2005 | Kantor .................. G01N 33/564 435/7.1 |
| 2005/0136489 A1 | 6/2005 | Tseng et al. |
| 2006/0135420 A1 | 6/2006 | Paz et al. |
| 2008/0145864 A1* | 6/2008 | Poynard .................. G01N 33/92 435/7.1 |
| 2008/0161203 A1 | 7/2008 | Su et al. |
| 2008/0194575 A1 | 8/2008 | Beraza et al. |
| 2008/0311593 A1 | 12/2008 | Younossi et al. |
| 2010/0291602 A1 | 11/2010 | Gangadharan et al. |
| 2011/0129859 A1 | 6/2011 | Tsubouchi et al. |
| 2012/0231471 A1* | 9/2012 | Sato ..................... A61K 31/232 435/7.1 |
| 2013/0137595 A1 | 5/2013 | Zangar et al. |
| 2013/0225428 A1 | 8/2013 | Qin et al. |
| 2013/0281309 A1 | 10/2013 | Meno et al. |
| 2014/0287948 A1* | 9/2014 | Boniface .............. G01N 33/689 506/18 |
| 2014/0302509 A1* | 10/2014 | Moerman .............. C12Q 1/686 435/7.1 |
| 2015/0045245 A1* | 2/2015 | Vanpoucke ........ G01N 33/6893 435/6.12 |
| 2015/0219672 A1 | 8/2015 | Meno et al. |
| 2016/0199416 A1 | 7/2016 | Lee et al. |
| 2016/0202274 A1 | 7/2016 | Gangadharan et al. |
| 2016/0356798 A1 | 12/2016 | Watkins |
| 2017/0199204 A1* | 7/2017 | Singbartl ........... G01N 33/6893 |
| 2018/0100867 A1 | 4/2018 | Okanoue et al. |
| 2020/0232034 A1* | 7/2020 | Kraus ................ G01N 33/6848 |

FOREIGN PATENT DOCUMENTS

| | | |
|---|---|---|
| CA | 2 777 013 A1 | 4/2011 |
| CN | 101275951 A | 10/2008 |
| CN | 101415836 A | 4/2009 |
| CN | 102625852 A | 8/2012 |
| CN | 105722858 A | 6/2016 |
| CN | 105765387 A | 7/2016 |
| CN | 105866423 A | 8/2016 |
| EP | 2799876 A2 | 11/2014 |
| KR | 20090042129 A | 4/2009 |
| WO | 2006121892 A2 | 11/2006 |
| WO | 2010000835 A1 | 1/2010 |
| WO | 2010079253 A2 | 7/2010 |

(Continued)

OTHER PUBLICATIONS

Extended European Search Report for Application No. 22165044.3, dated Dec. 16, 2022, pp. 1-22.

Tielong Chen et al., "Serum ficolin-2 concentrations are significantly changed in patients with hepatitis B virus infection and liver diseases", Virologica Sinica 2015, 30 (4): 249-260 DOI: 10.1007/s12250-015-3605-4, Aug. 2015 vol. 30 Issue 4 249-260.

Armstrong, MJ, P Gaunt, GP Aithal, D Barton, D Hull, R Parker, JM Hazlehurst, K Guo, G Abouda, MA Aldersley, D Stocken, SC Gough, JW Tomlinson, R Brown, SG Hübscher, PN Newsome, & Lean trial team 2016, 'Liraglutide safety and efficacy in patients with non-alcoholic steatohepatitis (Lean): a multicentre, double-blind, randomised, placebo-controlled phase 2 study', The Lancet, 2015, pp. 679-690, vol. 387, No. 10019, doi: 10.1016/j.ajg.2009.03.007.

(Continued)

*Primary Examiner* — Changhwa J Cheu
(74) *Attorney, Agent, or Firm* — Thomas|Horstemeyer, LLP

(57) ABSTRACT

The invention relates to methods of diagnosing, prognosing, or monitoring or staging the progression of non-alcoholic fatty liver disease (NAFLD) using biomarkers. The invention also relates to a method of scoring to determine the severity of NAFLD, and a method of treating NAFLD.

12 Claims, 7 Drawing Sheets

Specification includes a Sequence Listing.

(56) References Cited

FOREIGN PATENT DOCUMENTS

| WO | 2010081729 | A1 | | 7/2010 | | |
|---|---|---|---|---|---|---|
| WO | 2010133967 | A1 | | 11/2010 | | |
| WO | 2011046204 | A1 | | 4/2011 | | |
| WO | 2012/054870 | A2 | | 4/2012 | | |
| WO | 2008031051 | A2 | | 3/2013 | | |
| WO | WO-2014028494 | A1 | * | 2/2014 | ............ | C07K 16/40 |
| WO | 2015116880 | A1 | | 8/2015 | | |
| WO | 2015157697 | A1 | | 10/2015 | | |
| WO | 2016032319 | A1 | | 3/2016 | | |
| WO | 2016/086132 | A1 | | 6/2016 | | |
| WO | WO-2018007511 | A1 | * | 1/2018 | ............ | G01N 33/92 |

OTHER PUBLICATIONS

Banerjee, Rajarshi, Michael Pavlides, Elizabeth M. Tunnicliffe, Stefan K. Piechnik, Nikita Sarania, Rachel Philips, Jane D. Collier, Jonathan C. Booth, Jurgen E. Schneider, Lai Mun Wang, David W. Delany, Ken A. Fleming, Matthew D. Robson, Eleanor Barnes and Stefan Neubauer, "Multiparametric magnetic resonance for the non-invasivediagnosis of liver disease", European Association for the Study of the Liver: Joural of Hepatology, 2014, pp. 69-77, vol. 60, Elsevier B.V, doi: 10.1016/S0140-6736(15)00803-X.

Gangadharan, Bevin, Robin Antrobus, Raymond A. Dwek and Nicole Zitmann, "Novel Serum Biomarker Candidates for Liver Fibrosis in Hepatitis C Patients", Clinical Chemistry, 2007, pp. 1792-1799, vol. 53, No. 10, doi: 10.1373/clinchem.2007.089144.

Gangadharan, Bevin, Robin Antrobus, David Chittenden, Jan Rossa, Manisha Bapat, Paul Klenerman, Eleanor Barnes, Raymond A. Dwek and Nicole Zitmann, "New Approaches for Biomarker Discovery: The Search for Liver Fibrosis Markers in Hepatitis C Patients", Journal of Proteome Research, 2011, pp. 2643-2650, vol. 10, (American Chemical Society) ACS Publications, doi: 10.1021/pr101077c.

Gangadharan, Bevin and Nicole Zitmann, "Two dimensional gel electrophoresis using narrow pH 3-5.6 Immobilised pH gradient strips identifies potential novel disease biomarkers in plasma or serum", Nature Protocol Exchange, 2011, pp. 1-7, doi:10.1038/protex.2011.261.

Gangadharan, Bevin, Manisha Bapat, Jan Rossa, Robin Antrobus, David Chittenden, Bettina Kampa, Eleanor Barnes, Paul Klenerman, Raymond A. Dwek and Nicole Zitzmann, "Discovery of Novel Biomarker Candidates for Liver Fibrosis in Hepatitis C Patients: A Preliminary Study", PLoS One, 2012, pp. 1-14, vol. 7, No. 6, e39603, doi: 10.1371/journal.pone.0039603.

Kleiner, David E., Elizabeth M. Brunt, Mark Van Natta, Cynthia Behling, Melissa J. Contos, Oscar W. Cummings, Linda D. Ferrell, Yao-Chang Liu, Michael S. Torbenson, Aynur Unalp-Arida, Matthew Yeh, Arthur J. McCullough and Arun J. Sanyal, "Design and Validation of a Histological Scoring System for Nonalcoholic Fatty Liver Disease", Hepatology, 2005, pp. 1313-1321, vol. 41, No. 6, Wiley InterScience, doi: 10.1002/hep.20701.

Poynard, Thierry, Vlad Ratziu, Sylvie Naveau, Dominique Thabut, Frederic Charlotte, Djamila Messous, Dominique Capron, Annie Abella, Julien Massard, Yen Ngo, Mona Munteanu, Anne Mercadier, Michael Manns and Janice Albrecht, "The diagnostic value of biomarkers (SteatoTest) for the prediction of liver steatosis", Comparative Hepatology, 2005, pp. 1-14, vol. 4, No. 10, doi: 10.1186/1476-5926-4-10.

Petta, S., C. Cammà, D. Cabibi, V. Di Marco and A. Craxì, "Hyperuricemia is associated with histological liver damage in patients with non-alcoholic fatty liver disease", Alimentary Pharmacology and Therapeutics, 2011, pp. 757-766, vol. 34, Blackwell Publishing Ltd, doi: 10.1111/j.1365-2036.2011.04788.x.

Schwenzer, Nina F., Fabian Springer, Christina Schraml, Norbert Stefan, Jürgen Machmann and Fritz Schick, "Non-invasive assessment and quantification of liver steatosis by ultrasound, computed tomography and magnetic resonance", European Association for the Study of the Liver: Journal of Hepatology, 2009, pp. 433-445, vol. 51, Elsevier B.V., doi: 10.1016/j.jhep.2009.05.023.

Strauss, Simon, Ella Gavish, Paul Gottlieb and Ludmila Katsnelson, "Interobserver and Intraobserver Variability in the Sonographic Assessment of Fatty Liver", American Journal of Roentgenology (AJR), 2007, pp. W320-W323, vol. 189, American Roentgen Ray Society, doi: 10.2214/AJR.07.2123.

Yao, Wei, MM, Baozhen Zhao, MD, Yuhua Zhao, MD, Weiqi Wang, PhD and Guozheng Qian, PhD, "Ultrasonographic Texture Analysis of Parenchymatous Organs by the Four-Neighborhood-Pixels Algorithm", Journal of Ultrasound in Medicine, 2001, pp. 465-471, vol. 20, American Institute of Ultrasound in Medicine.

Haas, J. "Apolipoprotein F Affects Hepatic Phosphatidylcholine Metabolism and Is Reduced in Nash in Humans", Hepatology, 2016, p. 262, vol. 64, American Association for the Study of Liver Diseases.

Lee, Min-ho, Il Hong, Mingoo Kim, Byung-Hoon Lee, Ju-Han Kim, Kyung-Sun Kang, Hyung-Lae Kim, Byung-Il Yoon, Heekyoung Chung, Gu Kong and Mi-Ock Lee, "Gene expression profiles of murine fatty liver induced by the ad1ninistration of methotrexate", Toxicology, 2008, pp. 75-84, vol. 249, Elsevier B.V., doi: 10.1016/j.tox.2008.04.011.

Ahmed, Laila, Hosny Salama, Rasha Ahmed, Sherif Hamdy, Wafaa Al-Akel, Sanaa Abdel Shafi, Abeer Mahgoub, Amal Hareedy and Wael Fathy, "Non-invasive fibrosis seromarkers as a predictor of liver fibrosis in chronic hepatitis C and/or non-alcoholic steatohepatitis", Arab Journal of Gastroenterology, 2009, pp. 14-20, vol. 10, Elsevier B.V.

Bell, Lauren N., Janice L. Theodorakis, Raj Vuppalanchi, Romil Saxena, Kerry G. Bemis, Mu Wang and Naga Chalasani, "Serum Proteomics and Biomarker Discovery Across the Spectrum of Nonalcoholic Fatty Liver Disease", Hepatology, 2010, pp. 111-120, vol. 51, No. 1, doi: 10.1002/hep.23271.

Chunming, Li, Sheng Jianhui, Zhang Hongguang, Qiu Chunwu, Huang Xiaoyun, Yang Lijun and Yu Kuejun, "The development of a clinical score for the prediction of nonalcoholic steatohepatitis in patients with honalcoholic fatty liver disease using routine parameters", Turkish Journal of Gastroenterology, 2015, pp. 408-416, vol. 26, No. 5, The Turkish Society of Gastroenterology, doi: 10.5152/tJg.2015.6336.

Fitzpatrick, Emer and Anil Dhawan, "Noninvasive biomarkers in non-alcoholic fatty liver disease: Current status and a glimpse of the future", World Journal of Gastroenterology, 2014, pp. 10851-10863, vol. 20, No. 31, Baishideng Publishing Group Inc, doi: 10.3748/wjg.v20.i31.10851.

Kosone, T., H. Takagi, N. Horiguchi, Y. Ariyama, T. Otuska, N. Sohara, S. Kakizaki, K. Sato and M. Mori, "HGF ameliorates a high-fat diet-induced fatty liver", American Journal of Physiology-Gastrointestinal and Liver Physiology, 2007, pp. G204-G210, vol. 293, No. 1, doi: 10.1152/ajpgi.00021.2007.

Miller, Michael H., Shaun V. Walsh, Abdel Atrih, Jeffrey T-J Huang, Michael A J. Ferguson and John F. Dillon, "The serum proteome of nonalcoholic fatty liver disease: A multimodal approach to discovery of biomarkers of nonalcoholic steatohepatitis", Journal of Gastroenterology and Hepatology, 2014, pp. 1839-1847, vol. 29, No. 10, Wiley Publishing Asia Pty Ltd, doi: 10.1111/jgh.12614.

Poynard, Thierry, Vlad Ratziu, Frederic Charlotte, Djamila Messous, Mona Munteanu, Françoise Imbert-Bismut, Julien Massard, Luninita Bonyhay, Mohamed Tahiri, Dominique Thabut, Jean François Cadranel, Brigitte Le Bail, Victor De Ledinghen and the LIDO Study Group and the CYTOL Study Group, "Diagnostic value of biochemical markers (NashTest) for the prediction of non alcoholo steato hepatitis in patients with non-alcoholic fatty liver disease,", BMC (Boston Medical Center) Gastroenterology, 2006, pp. 1-16, vol. 6, No. 34.

Cuenca et al., Endocrine Practice 2014 col. 20, p. 18A-19A 11th Annual World Congress on Insulin Resistance, Diabetes and Cardiovascular Disease. Los Angeles CA (Year: 2014).

Ruiz et al. (Obesity Surgery 2007 17:1374-1380) (Year: 2007).

Smalling et al. (Am J. Physoil. Gastrointest LiverPhysoil. 2013 vol. 305: G364-374) (Year: 2013).

Kozik et al. (BMC Microbiology 2015 15:60) (Year: 2015).

Yoshimura et al., "Identification of Novel Noninvasive Markers for Diagnosing Nonalcoholic Steatohepatitis and Related Fibrosis by Data Mining", Hepatology 2016 vol. 63, pp. 462-473 (Year: 2016).

(56) References Cited

OTHER PUBLICATIONS

Chinese Office Action for Application No. 2017800656046, dated Jan. 5, 2022, pp. 1-19 (Translation Included).
Haiyan Huang et al., "Research advances in animal models of nonalcoholic fatty liver disease (in Chinese)", J Clin Hepatol, vol. 30 No. 9, Sep. 2014, pp. 948-953 (Abstract Included).
Partial European Examination Report for Application No. 22165044.3, dated Jul. 25, 2022, pp. 1-19.
Wong V W-S et al: "Bacterial endotoxin and non-alcoholic fatty liver disease in the general population: a prospective cohort study", Alimentary Pharmacology & Therapeutics, Blackwell Scientific Publications Ltd., Cambridge, GB, vol. 42, No. 6, Jul. 23, 2015 (Jul. 23, 2015), pp. 731-740.
Zharkova MS et al: "Serum Lipopolysaccharide-Binding Protein as a Marker of Bacterial Translocation and Increased Long-Term Mortality in Cirrhotic Patients P506 Prognostic Significance of the Hemodynamic and Clinical Staging in Patients With Chronic Liver Disease", The International Liver Congress(TM) 2014—49th Annual Meeting of the European Association for the Study of the Liver, Apr. 1, 2014 (Apr. 1, 2014), p. S238.

\* cited by examiner

CLINICAL DIAGNOSIS OF NON-ALCOHOLIC FATTY LIVER DISEASE USING A PANEL OF HUMAN BLOOD PROTEIN BIOMARKERS

CROSS-REFERENCE TO RELATED APPLICATIONS

This application is a Continuation of U.S. patent application Ser. No. 16/326,737, filed Feb. 20, 2019, which is the National Stage of International Application No. PCT/GB2017/052486, filed Aug. 23, 2017, which claims the priority to GB 1614455.2, filed Aug. 24, 2016, which are entirely incorporated herein by reference.

SEQUENCE LISTING

This application contains a sequence listing filed in electronic form as an ASCII.txt file entitled "Amended Sequence Listing N408344 JRN JCH[81].TXT", created on Tuesday, Dec. 2, 2022, and having a size of 13.9 kb. The content of the sequence listing is incorporated herein in its entirety.

FIELD OF INVENTION

The invention relates to methods of diagnosing, prognosing, or monitoring or staging the progression of non-alcoholic fatty liver disease (NAFLD) using biomarkers. The invention also relates to a method of scoring to determine the severity of NAFLD, and a method of treating NAFLD.

BACKGROUND TO THE INVENTION

NAFLD is the most common liver disorder in the Western world. It encompasses a disease spectrum of progressive liver disease ranging from non-alcoholic fatty liver (NAFL) to non-alcoholic steatohepatitis (NASH) which can develop with hepatic fibrosis and cirrhosis. The disease is associated with obesity and approximately 1 in 3 people in the US and UK have some degree of NAFLD and on average about 1 in 5 people worldwide. NAFLD is underdiagnosed since patients are usually asymptomatic even prior to the development of end-stage liver disease (ESLD).

The main stages of NAFLD comprise non-alcoholic fatty liver (NAFL), non-alcoholic steatohepatitis (NASH), hepatic fibrosis (liver fibrosis) and cirrhosis.

"Non-alcoholic fatty liver" or "NAFL" is also referred to as simple steatosis. It is where there is an accumulation of fat (triglycerides) and other lipids in the hepatocytes of the liver. Disordered fatty acid metabolism leads to steatosis and can be caused by various factors such as insulin resistance in diabetes, lack of exercise and excess food intake where there is an imbalance between calorific intake and combustion.

"Non-alcoholic steatohepatitis" or "NASH" is a more aggressive stage of NAFLD where there is hepatic inflammation accompanied with steatosis. In UK and Europe as many as 1 in 20 people have NASH. About 20% of patients undergoing liver transplants are patients with NASH. Cases of NASH are increasing in the general population including children and adolescents.

"Hepatic fibrosis" can be used interchangeably with "liver fibrosis". Hepatic fibrosis is a wound healing response characterized by the excessive accumulation of scar tissue (i.e. extracellular matrix) in the liver. Hepatic fibrosis may or may not be seen in NASH and is where normal structural elements of tissues are replaced with excessive amounts of non-functional scar tissue. Hepatic fibrosis can be caused by various factors including fatty liver, alcohol and viruses. Liver fibrosis is usually staged by severity using various staging methods such as Ishak, Metavir, Knodell and also the Kleiner-Brunt method for NAFLD.

"Hepatic cirrhosis" or "cirrhosis" is the most severe form of liver scarring and, unlike hepatic fibrosis, is nodular and causes irreversible architectural damage to the liver. Cirrhosis is the cause of over 6000 deaths every year in the UK and approximately 27,000 in the USA, making it the ninth leading cause of death. Cirrhosis is a major risk factor for hepatocellular carcinoma (HCC) and, at this stage of liver cancer, the only curative approach is liver transplantation. It is imperative to diagnose fibrosis in the early stages of reversible liver scarring so that irreversible liver damage in cirrhosis can be prevented.

The reference standard for assessing liver fibrosis and NAFLD is the liver biopsy and this invasive procedure has a number of well-known disadvantages: discomfort to the patient (pain and bleeding); it can be unreliable due to fibrosis being not homogenous throughout the liver; the false negative rate can be as high as 20%; an associated mortality rate of 1 in 10,000; inter-observer variability and high cost. Ultrasound can be used to diagnose NAFLD although the sensitivity of this approach is poor in clinically obese patients who are the most likely subjects to have NAFLD. Ultrasound also is unable to distinguish NASH and fibrosis within NAFLD and has low sensitivity for steatosis (Poynard et al., 2005, Comparative Hepatology, 4, 10; Yao et al., 2001, J Ultrasound Med, 20, 465; Schwenzer et al., 2009, J Hepatol, 51, 433). In a similar way to biopsy, ultrasound assessment of NAFLD is operator-dependent with an inter-observer variation (Strauss et al., 2007, Am J Roentgenol; 189, W320). Magnetic resonance imaging (MRI) is a promising approach to diagnose liver fibrosis (Banerjee et al., 2014, J Hepatol, 60, 69) which works for the majority of patients although it cannot be used for a very small number of patients who are claustrophobic, unable to keep still, unable to fit into the MRI scanner and for patients with internal medical devices such as pacemakers. Transient elastography (FibroScan) assesses liver stiffness and although this method is promising for liver fibrosis, it is difficult to perform in obese patients which make up most NAFLD patients (Petta et al., 2011, Aliment PharmacolTher, 33, 1350).

Consequently, there is a need for improved, minimally-invasive methods of determining stages of NAFLD in patients.

SUMMARY OF THE INVENTION

The inventors have identified protein biomarkers that are either up- or down-regulated in patients who are at different stages of NAFLD, such as NAFL, NASH with/without fibrosis, cirrhosis.

The invention provides a method of diagnosing, prognosing or monitoring or staging the progression of non-alcoholic fatty liver disease (NAFLD) in an individual, the method comprising detecting and quantifying one or more biomarkers in a biological sample obtained from the individual, wherein the one or more biomarkers is selected from apolipoprotein F, lipopolysaccharide-binding protein, ficolin-2, apolipoprotein D, kininogen-1, apolipoprotein M, thrombospondin-1, IgG Fc-binding protein, cystatin-c, alpha-1-acid glycoprotein 2, and leucine-rich alpha-2-glycoprotein, and thereby, diagnosing, prognosing or monitoring or staging the progression of NAFLD.

The invention further provides a method of scoring to determine the severity of NAFLD, the method comprising detecting and quantifying one or more biomarkers in a biological sample obtained from the individual, wherein the one or more biomarkers is selected from apolipoprotein F, lipopolysaccharide-binding protein, ficolin-2, apolipoprotein D, kininogen-1, apolipoprotein M, thrombospondin-1, IgG Fc-binding protein, cystatin-c, alpha-1-acid glycoprotein 2, and leucine-rich alpha-2-glycoprotein and wherein the level of biomarkers is compared to a control sample or reference sample/level to derive a score.

The invention additionally provides a method of treating NAFLD, the method comprising diagnosing NAFLD in an individual, by a method as described above and administering an agent or carrying out a treatment regimen effective to treat NAFLD to the individual.

The invention will now be described in more detail, by way of example and not limitation, and by reference to the accompanying drawings. Many equivalent modifications and variations will be apparent, to those skilled in the art when given this disclosure. Accordingly, the exemplary embodiments of the invention set forth are considered to be illustrative and not limiting. Various changes to the described embodiments may be made without departing from the scope of the invention as defined in the claims. All documents cited herein, whether supra or infra, are expressly incorporated by reference in their entirety.

The present invention includes the combination of the aspects and preferred features described except where such a combination is clearly impermissible or is stated to be expressly avoided. As used in this specification and the appended claims, the singular forms "a", "an", and "the" include plural referents unless the content clearly dictates otherwise. Thus, for example, reference to "a biomarker" includes two or more such biomarkers.

DETAILED DESCRIPTION

Figure 1:
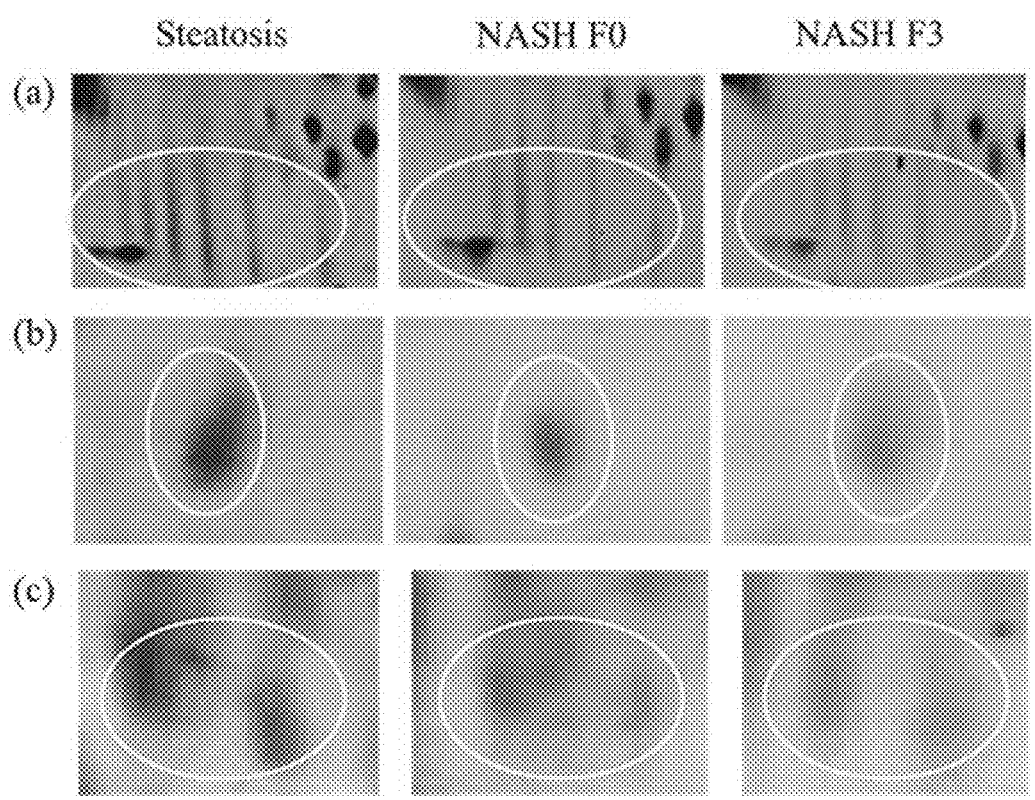
FIG. 1—Magnified regions of representative 2D-PAGE gels showing the decrease in expression of biomarkers across NAFLD stages. Three novel biomarkers are shown as an example and the relative position of the identified protein is circled. Stages of NAFLD from left to right are steatosis (NAFL), NASH with no fibrosis (F0) and NASH with advanced fibrosis (F3). (a) apolipoprotein D, (b) apolipoprotein M, (c) kininogen-1.

The present inventors have identified particular biomarkers that can be used alone or in combination in the diagnosis, prognosis or monitoring or staging the progression of non-alcoholic fatty liver disease (NAFLD). These biomarkers can be used in particular in staging NAFLD, to assess an individual as having non-alcoholic fatty liver (NAFL), non-alcoholic steatohepatitis (NASH), hepatic fibrosis and/or cirrhosis, associated with NAFLD. The identified biomarkers can be used in order to score the severity of NAFLD. These markers are also useful in methods comprising the diagnosis, monitoring or staging of NAFLD, and subsequently treating the individual, to treat NAFLD.

The present invention is directed to the analysis of one or more biomarkers in a sample taken from an individual. Typically, the sample is a blood sample, serum sample or plasma sample, although it may include cells, cell lysates, urine, amniotic fluid and other biological fluids. A blood sample may be capillary, venous or arterial blood or a plasma or serum sample. The sample may be a neat sample or extracted from a dried blood spot or other solid medium. Collection of samples may be performed using tubes (including vacutainers) or the sample can be blotted onto a solid medium such as dried blood spots (using capillary blood) on filter paper, cellulose membranes or the like. In the case of dried blood spots (DBS) this can be taken from a patient by pricking their finger with a lancet and transferring one or more drops of capillary blood onto a filter paper, cellulose membrane or equivalent sample support medium which allows easier sample handling and sample transportation as well as being more favored by the patient compared to venipuncture. Capillary blood could also be collected in specialized tubes such as the Microtainer, Microvette, Monovette, Minivette or Multivette.

The individual is typically a human subject. The individual may display one or more symptoms of NAFLD and/or may previously have been diagnosed with NAFLD, where the present methods are used in monitoring or staging of NAFLD. Additional parameters may have previously been used, or be used in combination with the methods of the present invention to aid in the assessment of NAFLD. Such parameters include patient age, patient gender, patient weight, patient height, body mass index (BMI), evidence of rapid weight loss/weight gain, eating habits, alcohol intake, medication records, patient exercise/activity history, ethnicity, and disease history (including history of diabetes including type II diabetes, cardiovascular disease, obesity, gastric bypass surgery, polycystic ovary syndrome, sleep apnoea, hypothyroidism, hypopituitarism, and metabolic syndrome which usually includes at least three of the following factors: increased waist circumference, hypertriglyceridemia, hypertension, high fasting glucose, and a low high-density lipoprotein (HDL) level).

In accordance with the present invention, one or more biomarkers are detected and quantified, at least one biomarker being typically selected from apolipoprotein F, lipopolysaccharide-binding protein, ficolin-2, apolipoprotein D, kininogen-1, apolipoprotein M, thrombospondin-1, IgG F C-binding protein, cystatin-C, alpha-1-acid glycoprotein 2, and leucine-rich alpha-2-glycoprotein.

The biomarkers, and their database accession number in the Uniprot database are listed below. The protein sequences as disclosed herein are with reference to the Uniprot sequence as of 31 Jul. 2016. Thus, below is a list of our biomarkers with their accession numbers (in parentheses) and alternative names (in italics):

apolipoprotein-F (Q13790) *Apo-F, Lipid transfer inhibitor protein, LTIP;*
apolipoprotein-M (095445) *Apo-M, ApoM, Protein G3a;*
apolipoprotein-D (P05090) *Apo-D, ApoD;*
kininogen-1 (P01042) *Alpha-2-thiol proteinase inhibitor, Fitzgerald factor, High molecular weight kininogen, HMWK, Williams-Fitzgerald-Flaujeac factor*
Kininogen-1 is Cleaved into the following 6 chains: 1) Kininogen-1 heavy chain, 2) T-kinin; Alternative name(s): Ile-Ser-Bradykinin, 3) Bradykinin; Alternative name(s): Kallidin I, 4) Lysyl-bradykinin, Alternative name(s): Kallidin II, 5) Kininogen-1 light chain, 6) Low molecular weight growth-promoting factor;
ficolin-2 (Q15485) *37 kDa elastin-binding protein, Collagen/fibrinogen domain-containing protein 2, EBP-37, Ficolin-B, Ficolin-beta, Hucolin, L-ficolin, Serum lectin p35;*
thrombospondin-1 (P07996);
IgG Fc-binding protein (Q9Y6R7) *Fcgamma-binding protein antigen, FcgammaBP*
cystatin-c (P01034) *Cystatin-3, Gamma-trace, Neuroendocrine basic polypeptide, Post-gamma-globulin;*
lipopolysaccharide-binding protein (P18428) *LBP;*
alpha-1-acid glycoprotein 2 (P19652) *AGP 2, Orosomucoid-2, OMD 2;* and
leucine-rich alpha-2-glycoprotein (P02750) *LRG.*

In accordance with the present invention, the inventors have identified that levels of certain of these proteins decrease with increasing NAFLD severity. In particular, apolipoprotein F, alpha-1-acid glycoprotein 2, ficolin-2 and leucine-rich alpha-2-glycoprotein all demonstrate decreasing levels of protein with increasing NAFLD severity. In contrast, levels of cystatin C, lipopolysaccharide-binding protein, IgG Fc-binding protein and thrombospondin-1 show increasing levels with increasing NAFLD severity.

In a preferred aspect of the present invention, the one or more marker is selected from apolipoprotein F, apolipoprotein D, kininogen-1, ficolin-2, apolipoprotein M and thrombospondin-1. A particularly preferred biomarker is apolipoprotein F.

Apolipoprotein F shows a decrease in concentration with increasing NAFLD severity. Accordingly, monitoring changes in the level of this protein in an individual provides an indication of the progress of NAFLD through the stages.

Apolipoprotein D demonstrates high levels in healthy controls, and consistency lower levels in all stages of NAFLD. Accordingly, this marker can be used as an early NAFLD biomarker. A decreasing level of apolipoprotein D, as compared with a control sample or reference sample/level, indicates increasing severity of NAFLD. Apolipoprotein M shows a slight decrease from steatosis (NAFL) to NASH F0, but reduces an expression in NASH F3. Accordingly, apolipoprotein M is useful in determining progress to hepatic fibrosis. Kininogen-1 shows a consistent decrease across all NAFLD stages.

Ficolin-2 shows a decrease in NAFLD stages, showing its lowest levels in fibrosis stage F3.

Thrombospondin-1 increases from control levels to steatosis (NAFL) and across all stages of NAFLD.

In a preferred aspect of the present invention, the at least one biomarker comprises apolipoprotein F, lipopolysaccharide-binding protein, and/or ficolin-2. In an additional preferred aspect of the invention, the at least one biomarker comprises apolipoprotein F, lipopolysaccharide-binding protein, ficolin-2, and/or apolipoprotein D.

In another preferred aspect of the present invention, the present invention provides for analysis of at least two, at least three, at least four or at least five or more biomarkers and thereby, diagnosing, prognosing or monitoring or staging the progression of NAFLD. Thus, the biomarkers identified above are preferably used in combination with one or more additional biomarkers.

For example, a combination of markers can be used to provide more precise staging of NAFLD. Such biomarkers may be selected from apolipoprotein F, lipopolysaccharide-binding protein, ficolin-2, apolipoprotein D, kininogen-1, apolipoprotein M, thrombospondin-1, IgG Fc-binding protein, cystatin-c, alpha-1-acid glycoprotein 2, and leucine-rich alpha-2-glycoprotein. A combination of markers used in accordance with the invention preferably comprises the biomarker apolipoprotein F and one or more additional biomarkers selected from lipopolysaccharide-binding protein, ficolin-2, apolipoprotein D, kininogen-1, apolipoprotein M, thrombospondin-1, IgG Fc-binding protein, cystatin-c, alpha-1-acid glycoprotein 2, and leucine-rich alpha-2-glycoprotein. A preferred combination comprises apolipoprotein F and one or more, such as two, three or four additional biomarkers selected from lipopolysaccharide-binding protein, ficolin-2, apolipoprotein D, alpha-1-acid glycoprotein 2 and thrombospondin-1.

Additional combinations of markers that may be used in accordance with the invention include (i) one or more biomarkers selected from apolipoprotein F, lipopolysaccharide-binding protein, and ficolin-2, in combination with one or more biomarkers selected from apolipoprotein D, alpha-1-acid glycoprotein 2 and thrombospondin-1; and (ii) one or more biomarkers selected from apolipoprotein F, lipopolysaccharide-binding protein, and ficolin-2, in combination with one or more biomarkers selected from apolipoprotein D, alpha-1-acid glycoprotein 2 and thrombospondin-1. Alternatively, additional biomarkers may be combined with the one or more biomarkers of the invention.

In a preferred aspect of the present invention, the method comprises analysis of at least apolipoprotein F and lipopolysaccharide-binding protein; apolipoprotein F and ficolin-2; apolipoprotein F and apolipoprotein Dlipopolysaccharide-binding protein and ficolin-2; lipopolysaccharide-binding protein and apolipoprotein D; apolipoprotein D and ficolin-2; apolipoprotein F, lipopolysaccharide-binding protein and ficolin-2; or apolipoprotein F, apolipoprotein D, lipopolysaccharide-binding protein and ficolin-2

The present methods may be used in the diagnosis of NAFLD, or in the prognosis of NAFLD, for example, to establish the severity of disease. In a preferred aspect of the present invention, the methods can be used in the staging of NAFLD, and in particular, in the staging of the individual as suffering from non-alcoholic fatty liver (NAFL), also referred to as steatosis. A preferred biomarker for early staging of NAFLD and staging as NAFL is apolipoprotein D. The methods may also be used to stage NAFLD as non-alcoholic steatohepatitis (NASH). A preferred biomarker for staging severity of NAFLD and staging as NASH is apolipoprotein M. The methods may also be used to stage the individual as suffering from hepatic fibrosis, including the severity of fibrosis.

In a further aspect of the present invention, in addition to the analysis of the one or more biomarkers as disclosed above, the invention also provides the analysis of one or more further biomarkers. The one or more further biomarkers may be selected from the further biomarkers identified according to the invention as described below.

The one or more further biomarkers may comprise keratin type I cytoskeletal 18, accession number in parentheses; alternative names in italics: (P05783) *Cell proliferation-inducing gene 46 protein, Cytokeratin-18, CK-18, Keratin-18, K18* and/or adiponectin (Q15848) *30 kDa adipocyte complement-related protein, Adipocyte complement-related 30 kDa protein, ACRP30, Adipocyte, C1q and collagen domain-containing protein, Adipose most abundant gene transcript 1 protein, apM-1, Gelatin-binding protein.*

Adiponectin is a particularly preferred further biomarker. The results described herein show that adiponectin decreases in concentration from control to steatosis (NAFL) to NASH, but is constant in the fibrosis stages of NASH. Accordingly, this is a useful early marker for NAFL and progression to NASH. A decreasing level of adiponectin, as compared with a control sample or reference sample/level, thus indicates increasing severity of NAFLD as it progresses up to the non-alcoholic steatohepatitis stage.

Accordingly, a method of the present invention may comprise analysis of at least apolipoprotein F and adiponectin; lipopolysaccharide-binding protein and adiponectin; ficolin-2 and adiponectin; apolipoprotein D and adiponectin; apolipoprotein F, apolipoprotein D and adiponectin; apolipoprotein F, lipopolysaccharide-binding protein and adiponectin; apolipoprotein F, ficolin-2 and adiponectin; lipopolysaccharide-binding protein, ficolin-2 and adiponectin; apolipoprotein D, lipopolysaccharide-binding protein and adiponectin; apolipoprotein D ficolin-2 and adiponectin; or apolipoprotein F, lipopolysaccharide-binding protein, ficolin-2 and adiponectin.

The invention also provides for the assessment of cleavage products of one or more proteins. Suitable proteins for analysis of cleavage products include kininogen-1, keratin type I cytoskeletal 18, and angiotensinogen. Typically, the amount of cleavage products for these peptides increases with severity of NAFLD, such that monitoring of levels of the cleavage products can be used as part of the methods of the present invention.

The present methods can also be used to monitor the progress of NAFLD, for example, in a patient diagnosed with NAFLD. The method can be repeated at suitable intervals, such as once a month, once every two months, once every three months, once every six months, once a year, once every two years or once every three years in order to monitor the progress of NAFLD, and in particular, to monitor changes in the biomarker(s), associated with progression to a different stage of NAFLD. Such monitoring can also be used in assessment of the effectiveness of therapy for such patients.

The one or more biomarkers of the present invention can be assessed by any suitable technique, including for example immunoassays. In a particularly preferred aspect of the present invention, the methods use mass spectrometry to assess the one or more biomarkers.

In specific embodiments, the one or more biomarkers are quantified using antibody-free approaches such as, but not limited to, Parallel Reaction Monitoring (PRM), Selected Reaction Monitoring (SRM), Multiple Reaction Monitoring (MRM) or multi-stage fragmentation in MRM-cubed (MRM$^3$) using mass spectrometry.

The biological sample (either capillary/venous/arterial blood, serum or plasma) is digested with a protease such as, but not limited to, trypsin, chymotrypsin, Arg-C, Asp-N, clostripain, elastase, Glu-C, Lys-C, Lys-N, pepsin, protein endopeptidase and Staphylococcus protease, but in specific embodiments the enzyme is trypsin. In the case of trypsin, this also includes immobilized trypsin for higher throughput digestion such as Flash digest from Perfinity Biosciences (also called SMART Digest from Thermo Scientific). The cleavage properties of these enzymes are known (for example, trypsin cleaves after lysine, K or arginine, R) and so the resulting peptides are determined manually or using a software (such as Skyline, PinPoint etc) to digest the proteins in-silico. Typically peptides shorter than 7 amino acids are excluded since they are unlikely to be unique. Typically peptides longer than 25 amino acids are excluded since synthetic peptides as standards are likely to be expensive. Although peptides between 7 to 25 amino acids are typically selected for analysis, peptides shorter than 7 amino acids and longer than 25 amino acids should not be entirely excluded. When using trypsin, typically peptides with no missed cleavages are selected but peptides with one or more missed cleavages can be considered for any enzyme. Typically the peptides are selected which are not modified (e.g glycosylated, phosphorylated, etc) and methionine, M, is avoided since this amino acid may or may not be oxidized and these modifications would change the mass of the peptide. Modified peptides should not be entirely excluded if the mass of the modification (e.g. glycosylation, phosphorylation, oxidation, carbamidomethylation etc) is known.

Online databases such as, but not limited to, PeptideAtlas and the Global Proteome Machine database (gpmdb), help to determine the commonly observed peptides for the proteins of interest. MRMaid can be used to help design assays for mass spectrometry based targeted quantitation by suggesting peptides and MS$^2$ ions to monitor based on experimental spectra from the PRIDE database. Protein BLAST is used to check the uniqueness of the selected peptide. If a peptide is not unique, then another peptide within the biomarker sequence would be selected.

Prior to mass spectrometry, digested peptides can be fractionated using phosphopeptide enrichment, glycopeptide enrichment, high pH reversed phase fractionation or the like. Peptides can be separated by reversed phase liquid chromatography, hydrophilic interaction liquid chromatography (HILIC), ion-exchange chromatography, isoelectric focusing or the like but in specific embodiments separation is by reversed phase liquid chromatography using a carbon-18 (C-18) column. In the case of very low abundant biomarkers, samples can be fractionated using pH based reversed-phase fractionation, biomarkers could be enriched using immunoprecipitation or high abundant proteins could be depleted (using immunoprecipitation or dye-affinity methods such as Cibacron-blue for the depletion of albumin in serum and/or plasma samples).

SRM/MRM is performed using a triple quadrupole mass spectrometer. The first quadrupole filters the preselected peptide (MS$^1$ ion) of the protein of interest, the second quadrupole fragments this peptide and the third quadrupole filters a fragment or fragments ($MS^2$ ions) of the peptide for detection. PRM is performed using a hybrid quadrupole-Orbitrap mass spectrometer such as a Thermo Q Exactive and its variants or a Thermo Fusion and its variants. In PRM, the quadrupole filters the preselected peptide ($MS^1$ ion) of the protein of interest, the higher-energy collisional dissociation (HCD) cell fragments this peptide and the Orbitrap is able to detect all fragments ($MS^2$ ions) of the peptide due to its high resolution. $MRM^3$ is performed using a QTRAP mass spectrometer. In $MRM^3$, the first quadrupole filters the preselected peptide ($MS^1$ ion) of the protein of interest, the second quadrupole fragments this peptide, then the fragment ions ($MS^2$ ions) are trapped after being isolated in the linear ion trap followed by excitation to perform a second fragmentation step with $MS^3$ ions to give a higher level of sensitivity. In specific embodiments, the technique includes any tandem mass spectrometer capable of MS/MS with sample ionization carried out using electrospray ionization (ESI) but may also be performed using other ionization methods.

The area under the curve (AUC) of the fragment ions can be used to relatively quantify the levels of the proteins. Known amounts of synthetic pure heavy-labelled peptides with the same sequence as the preselected peptides can be used to establish a calibration curve to help determine the absolute concentration of the proteins. In more detail, detection of these peptides can be carried out using SRM, MRM, $MRM^3$, PRM or the like where a mass spectrometer filters for the preselected peptide ($MS^1$ ion), fragments the peptide and the peptide fragments ($MS^2$ ions) are detected. The AUC for these $MS^2$ ions are used to quantify the biomarkers. For absolute quantitation, known amounts of synthetic peptides are used which can be isotopically labelled. Synthesis is typically performed from the C-terminus to the N-terminus of the peptide. The synthesis cycle comprises: a) Loading of the C-terminal amino acid to the solid support phase (polystyrene resin). This amino acid is protected at the N-terminus to avoid unwanted reactions; b) Removal of N-terminal protection group (PG) of this amino acid; c) Activation of C-terminus of the next amino acid (N-terminus carries protection group); d) Coupling reaction of these two amino acids; e) Re-start of cycle at b) or cleavage of full-length peptide from resin. Peptides can be crude or having a purity of at least 70%, at least 75%, at least 80%, at least 85%, at least 90%, at least 95% or at least 98%. Peptides can be synthetic peptides, IGNIS peptides, PEPotec peptides, AQUA peptides, SpikeTide peptides, Protein Epitope Signature Tag (QPrEST) peptides, microwave-assisted solid phase synthesized peptides, concatenated signature peptides encoded by QconCAT genes or the like. Both detection and/or enrichment of the endogenous peptides in the biological sample can be achieved using anti-peptide antibodies, Stable Isotope Standard Capture with Anti-Peptide Antibodies (SISCAPA) or the like where the anti-peptide antibody is raised against the preselected peptide. In addition to isotopically labelled peptides, quantitation of biomarkers can also be achieved by label-free mass spectrometry based quantitation (using the Progenesis LC-MS software, Skyline software or the like) or by labelling the proteins in the biological samples using isotope tags such as tandem mass tags (TMT), isobaric tags for relative and absolute quantitation (iTRAQ), isotope-coded affinity tags (ICAT) or the like.

Absolute quantitation can be carried out using the Heavy-Peptide IGNIS Prime Custom Peptide Quantitation Kit from Life Technologies with the digestion of IGNIS Prime peptides using either trypsin or immobilized trypsin such as Flash digest from Perfinity Biosciences (also called SMART Digest from Thermo Scientific).

Using apolipoprotein F (APO-F) as an example the workflow for peptide selection is described and this can be followed for any of the biomarkers listed. The unprocessed precursor of APO-F has 326 amino acids. Amino acids 1-35 are for a signal peptide, amino acids 36-164 are for a propeptide and amino acids are for the functional APO-F. In-silico digestion of the functional APO-F sequence shows four peptides which are between the criteria of 7 to 25 amino acids: SLPTEDCENEK (SEQ ID NO: 1) (m/z 661.2825, 2+ or m/z 441.1907, 3+), SGVQQLIQYYQDQK (SEQ ID NO: 2) (m/z 849.4283, 2+ or m/z 566.6213, 3+), DANISQPETTK (SEQ ID NO: 3) (m/z 602.2962, 2+, m/z 401.8666, 3+), SYDLDPGAGSLEI (SEQ ID NO: 4) (m/z 668.8170, 2+, m/z 446.2138, 3+). All these peptides can be targeted by mass spectrometry using SRM, MRM, PRM, $MRM^3$ or the like by targeting the $MS^1$ ions shown above in parentheses. In the case of DANISQPETTK (SEQ ID NO: 3), the second threonine, T, in its sequence is O-glycosylated and so would not normally be chosen as a suitable peptide. However, DANISQPETTK (SEQ ID NO: 3) should not be ruled out if the protein is deglycosylated.

In addition to the detection of the biomarkers themselves, in some embodiments, the methods of the invention are directed to the detection of fragments of the particular biomarkers. For example, some proteins such as keratin type I skeletal 18 and kininogen-1 are cleaved, with the level of cleavage increasing in NAFLD. Accordingly, for these proteins, monitoring for the cleavage products provides a marker for NAFLD and/or the stage of disease. In preferred embodiments, cleavage products are detected by mass spectrometry methods. When detecting cleavage products, the initial protease digestion step may not be conducted.

In the case of keratin type I cytoskeletal 18, this protein is cleaved by a caspase between amino acids 397/398 of the complete unprocessed sequence (i.e. between amino acids 396/397 of the functional keratin type I cytoskeletal 18 after the initiator methionine is removed) and this cleavage increases with NAFLD. The tryptic peptide LLEDGEDFNLGDALDSSNSMQTIQK (SEQ ID NO: 5) covers this cleavage region and can be targeted by mass spectrometry using SRM, MRM, PRM, $MRM^3$ or the like. The three serine (S) amino acids in the sequence are known to be phosphorylated and methionine (M) could be oxidized so the m/z of this peptide should be calculated if these four amino acids are both modified and unmodified. Levels of this peptide decrease with increasing NAFLD severity. In addition the cleaved tryptic peptide LLEDGEDFNLGDALD (SEQ ID NO: 6) can be targeted by mass spectrometry using SRM, MRM, PRM, $MRM^3$ or the like by targeting a peptide of m/z 818.3729, 2+ or m/z 545.9177, 3+. Levels of this peptide increase with increasing NAFLD severity. The cleaved tryptic peptide SSNSMQTIQK (SEQ ID NO: 7) can also be targeted by mass spectrometry using SRM, MRM, PRM, $MRM^3$ or the like and also increase with increasing NAFLD severity although as before the m/z of this peptide should be calculated if the serine (S) and methionine (M) amino acids are both modified and unmodified.

Kininogen-1 was found to be a novel biomarker for NAFLD. Kininogen-1 cleaves into the following 6 chains all of which may be potential biomarkers for NAFLD: kininogen-1 heavy chain, T-kinin, bradykinin, lysyl-bradykinin, kininogen-1 light chain and low molecular weight growth-promoting factor. T-kinin (sequence ISLMKRPPGFSPFR (SEQ ID NO: 8); m/z 816.9558, 2+; m/z 544.9729, 3+), bradykinin (sequence RPPGFSPFR (SEQ ID NO: 9); m/z 530.7880, 2+; m/z 354.1944, 3+) and lysyl-bradykinin (sequence KRPPGFSPFR (SEQ ID NO: 10); m/z 594.8355, 2+; m/z 396.8927, 3+) are short peptides which can be targeted by mass spectrometry using either SRM, MRM, PRM, MRM$^3$ or the like. These sequences are targeted without predigesting the sample with trypsin or other enzymes. Bradykinin is released from kininogen by plasma kallikrein. Hydroxylation of the second proline (P) in the sequences above (RPP[+16]GFSPFR (SEQ ID NO: 9); m/z 538.7854, 2+; m/z 359.5236, 3+) occurs prior to the release of bradykinin which would additionally need to be considered for MS$^1$ ion selection.

In a similar way to keratin type I cytoskeletal 18 and kininogen-1, peptides for other proteins which cleave with fatty liver and/or fibrosis can be selected which cover the cleavage regions and are on either side of the cleavage region. For example, alpha 2 macroglobulin and cleaved/intact complement C3 are proteins with a fibrosis-dependent thioester cleavage region.

Hemoglobin A1c (HbA1c, glycated hemoglobin) is a component of hemoglobin which binds glucose and elevated levels indicate poor glucose control over 6-8 weeks in diabetics. Type II diabetes is a risk factor in NAFLD and so HbA1c levels can also be measured in addition to the biomarkers disclosed herein. In HbA1c, glucose is attached to the N terminal valine (V) of the hemoglobin beta chain. Unprocessed hemoglobin beta chain is 147 amino acids in length and the first amino acid is an initiator methionine which is removed. The remaining amino acids from 2-147 make up the functional hemoglobin beta chain. The valine (V) amino acid in position 2 is the glycation site for HbA1c. HbA1c is usually measured in the clinic by HPLC but could also be analyzed by targeted mass spectrometry using SRM, MRM, PRM, MRM$^3$ or the like. If the proteins in a biological sample from a NAFLD or diabetic patient are digested with trypsin, the N terminal peptide from hemoglobin beta chain has the sequence VHLTPEEK (SEQ ID NO: 11) (m/z 476.7585, 2+; m/z 318.1748, 3+) which can be targeted by mass spectrometry. The presence of this peptide at m/z 476.7585 (2+) or m/z 318.1748 (3+) would indicate hemoglobin beta chain which is not glycated at the N terminal valine (V) whereas the absence of this peptide would suggest glycation of hemoglobin beta chain at the N terminal valine (V). The glycated peptide will have additional mass of glucose (with loss of one water molecule) with the sequence V[+162.1]HLTPEEK (SEQ ID NO: 11) (m/z 557.7850, 2+; m/z 372.1924, 3+). This can be used to assess glucose control in a patient and for monitoring type II diabetes which is a major risk factor for NAFLD. This approach can also be used to check other glycation sites in hemoglobin alpha and beta chains as well as other proteins.

Angiotensinogen is also a biomarker of fibrosis. The following peptide hormones are derived from angiotensinogen: angiotensin-1 (DRVYIHPFHL (SEQ ID NO: 12); m/z 648.8460, 2+; m/z 432.8998, 3+), angiotensin 1-9 (DRVYIHPFH (SEQ ID NO: 13); m/z 592.3040, 2+; m/z 395.2051, 3+), angiotensin-2 (DRVYIHPF (SEQ ID NO: 14); m/z 523.7745, 2+; m/z 349.5188, 3+), angiotensin 1-7 (DRVYIHP (SEQ ID NO: 15); m/z 450.2403, 2+; m/z 300.4960, 3+), angiotensin 1-5 (DRVYI (SEQ ID NO: 16); m/z 333.1845, 2+; m/z 222.4588, 3+; not unique and too short), angiotensin 1-4 (DRVY (SEQ ID NO: 17); m/z 276.6425, 2+; m/z 184.7641, 3+; not unique and too short), angiotensin-3 (RVYIHPF (SEQ ID NO: 18); m/z 466.2611, 2+; m/z 311.1765, 3+) and angiotensin-4 (VYIHPF (SEQ ID NO: 19); m/z 388.2105, 2+; m/z 259.1428, 3+). Angiotensin-2 is a known hepatic stellate cell activator in liver fibrosis. These peptides can be targeted by mass spectrometry using either SRM, MRM, PRM, MRM$^3$ or the like. These sequences must be targeted without predigesting the sample with trypsin or other enzymes.

Since the peptides from kininogen-1 and angiotensinogen are liberated naturally from their processing, they can be detected without the need for cleavage with enzyme (e.g. trypsin, chymotrypsin etc). The peptides can be detected from the biological sample by removal of proteins with a higher molecular weight using chromatography, molecular weight cut off filters, size exclusion or the like and then targeting the peptide by mass spectrometry.

The detection methods of the invention may also comprise use of an agent wherein the agent specifically detects proteins or peptides of interest. The agent could be an antibody or functional equivalent thereof that binds proteins or peptides under analysis (i.e. anti-peptide antibody). These antibodies may be used to perform an immunoassay such as, but not limited to, enzyme linked immunosorbent assay (ELISA), radio-immunoassay, protein dot blot, Western blot, turbidimetry, nephelometry and the like. The kit may further comprise at least one target specifically for detecting another gene or gene product useful as a prognostic indicator.

The biomarkers may also be detected by suitable immunoassay using agents that specifically bind the marker of interest. Such binding agents include immunoglobulins and functional equivalents of immunoglobulins that specifically bind to the biomarkers of interest. The terms "immunoglobulin" and "antibody" are used interchangeably and in their broadest sense herein. Thus, they encompass intact monoclonal antibodies, polyclonal antibodies, antibody phage display (APD), multispecific antibodies (e.g., bispecific antibodies) formed from at least two intact antibodies, and antibody fragments, so long as they exhibit the desired biological activity. APD involves bacteriophage genetic engineering and multiple rounds of phage propagation and antigen guided selection.

In addition to using antibodies to detect the biomarkers, antibodies can also be used to enrich the biomarkers in the biological sample to help with other detection/quantitation methods. This includes techniques such as immunoprecipitation using Protein A, Protein G, Protein A/G or streptavidin/avidin beads for biotinylated antibodies. Using immunoprecipitation antibodies against the target biomarkers could optionally be crosslinked onto the beads using a crosslinker such as disuccinmidyl suberate (DSS) to avoid the presence of the antibody in the elution. Alternatively Mass Spectrometric Immunoassay (MSIA) can be used for downstream mass spectrometry analysis of NAFLD-ASSOCIATED biomarkers using SRM, MRM, MRM$^3$, PRM or the like. MSIA tips could have either Protein A, Protein G or Protein A/G for the capture of antibodies to the target biomarker. MSIA tips could have streptavidin or avidin for the capture of biotinylated antibodies to the target biomarker. MSIA is particular useful for very low abundant biomarkers which cannot be usually detected without enrichment (such as keratin type I cytoskeletal 18).

The invention further provides methods for detecting the presence of and/or measuring a level of one or more biomarkers of interest in a biological sample, using an antibody specific for the biomarker of interest. Specifically, the method for detecting the presence of the biomarker of interest in a biological sample may comprise the step of contacting the sample with a monoclonal antibody and detecting the binding of the antibody with the biomarker in the sample. More specifically, the antibody may be labeled so as to produce a detectable signal using compounds including, but not limited to, a radiolabel, an enzyme, a chromophore and a fluorophore.

Detection of specific binding of an antibody specific for the protein of interest, or a functional equivalent thereof, when compared to a suitable control, is an indication that the biomarker is present in the sample. Suitable controls include a sample known not to contain the proteins of interest and a sample contacted with an antibody not specific for the encoded protein, e.g., an anti-idiotype antibody. A variety of methods to detect specific antibody-antigen interactions are known in the art and may be used in the method, including, but not limited to, standard immunohistological methods, immunoprecipitation, an enzyme immunoassay, and a radioimmunoassay. In general, the specific antibody will be detectably labeled, either directly or indirectly. Direct labels include radioisotopes; enzymes whose products are detectable (e.g., luciferase, 3-galactosidase, and the like); fluorescent labels (e.g., fluorescein isothiocyanate, rhodamine, phycoerythrin, and the like); fluorescence emitting metals (e.g., 112Eu, or others of the lanthanide series, attached to the antibody through metal chelating groups such as EDTA); chemiluminescent compounds (e.g., luminol, isoluminol, acridinium salts, and the like); bioluminescent compounds (e.g., luciferin, aequorin (green fluorescent protein), and the like). The antibody may be attached (coupled) to an insoluble support, such as a polystyrene plate or a bead. Indirect labels include second antibodies specific for antibodies specific for the encoded protein ("first specific antibody"), wherein the second antibody is labeled as described above; and members of specific binding pairs, e.g., biotin-avidin, and the like. The biological sample may be brought into contact with and immobilized on a solid support or carrier, such as filter paper, nitrocellulose membrane or cellulose membrane, that is capable of immobilizing cells, cell particles, or soluble proteins. The support may then be washed with suitable buffers or solvents (such as acetone to dissolve the cellulose membrane and precipitate the proteins in the biological sample), followed by digesting the proteins in the sample to peptides using enzymes and then detecting and quantifying the biomarkers by mass spectrometry or contacting with a detectably-labeled first specific antibody. Detection methods are known in the art and will be chosen as appropriate to the signal emitted by the detectable label. Detection is generally accomplished in comparison to suitable controls and to appropriate standards.

The detection methods of the invention may also comprise use of an agent to detect changes in post-translational modifications of the biomarkers in NAFLD and across NAFLD stages. These post-translational modifications may include N-glycosylation, O-glycosylation and phosphorylation.

In another embodiment, the current invention provides a method of determining the prognosis of NAFLD/fibrosis, comprising: (a) determining the level of a protein selected from apolipoprotein F, lipopolysaccharide-binding protein, ficolin-2, apolipoprotein D, kininogen-1, apolipoprotein M, thrombospondin-1, IgG Fc-binding protein, cystatin-c, alpha-1-acid glycoprotein 2, and leucine-rich alpha-2-glycoprotein in a biological sample obtained from a patient; and (b) comparing said level of (a) to a control level of said protein in order to determine a positive or negative diagnosis of said fatty liver or fibrosis.

Methods of Therapy

In some cases in accordance with the invention, a method of treating NAFLD is described. The method comprises diagnosing NAFLD in an individual, detecting and quantifying one or more biomarkers in a biological sample obtained from the individual, wherein the one or more biomarkers is selected from apolipoprotein F, lipopolysaccharide-binding protein, ficolin-2, apolipoprotein D, kininogen-1, apolipoprotein M, thrombospondin-1, IgG Fc-binding protein, cystatin-c, alpha-1-acid glycoprotein 2, and leucine-rich alpha-2-glycoprotein administering an agent to the individual or carrying out a treatment regimen on the individual and thereby treating NAFLD.

The individual typically has NAFLD, i.e. has been diagnosed as having NAFLD, or is suspected as having NAFLD, i.e. shows the symptoms of NAFLD. As used herein, the term "treating" includes any of following: the prevention of the disease or of one or more symptoms associated with the disease; a reduction or prevention of the development or progression of the disease or symptoms; and the reduction or elimination of an existing disease or symptoms. Treatments of NAFLD/NASH are aimed at reducing liver-related and all-cause (specifically cardiovascular) morbidity and mortality. Selection of a treatment approach requires assessment of liver disease severity. Treatment strategies that may be used according to the invention include (i) lifestyle intervention or other weight loss regime, aiming for weight loss of >7; and (ii) treatments optimising cardiovascular risk factors, including glucose control in diabetics, blood pressure control, or lipid-lowering therapy.

Agents that may be administered for treatment include angiotensin converting enzyme inhibitors (ACE-I)/angiotensin receptor blockers (ARBs), which have potential antifibrotic effects, and metformin which may reduce risk of liver cancer. Liraglutide is a further agent that may be used for treatment, which appears to improve NASH beyond its effect on weight loss (LEAN study, Armstrong et al. Lancet 2015). Liver specific therapeutic agents (such as those in phase 3 clinical trials) aimed at those patients with NASH and more advanced fibrosis (F2-3) may also be used. Examples include Obeticholic acid, a synthetic bile acid derivative (Intercept pharmaceuticals), Elafibranor, a PPAR a/d agonist (Genfit). There are currently a number of other drug candidates at various stages of development which may be used. A further treatment strategy which may be used in an individual diagnosed with NAFLD is surgical intervention. For example, bariatric surgery (sleeve gastrectomy or roux-en-y gastric bypass) in morbidly obese patients.

Specific routes, dosages and methods of administration of the therapeutic agents described herein may be routinely determined by the medical practitioner. These are discussed in more detail below.

Agent

The agents for use in the methods of treatment described herein may be formulated in pharmaceutical compositions. These compositions may comprise, in addition to the therapeutically active ingredient(s), a pharmaceutically acceptable excipient, carrier, diluent, buffer, stabiliser or other materials well known to those skilled in the art. Such materials should be non-toxic and should not interfere with the efficacy of the active ingredient. The pharmaceutical carrier or diluent may be, for example, an isotonic solution.

Kits

The invention further provides a kit that comprises means (e.g. reagents) for detecting and quantifying one or more biomarkers described herein in a biological sample from an individual and instructions for use of the kit in accordance with methods of the invention. The kit may also comprise details regarding which individuals the method may be carried out upon. The kit typically contains one or more agents, (e.g. an antibody) that specifically bind to the relevant biomarker(s). The kit may additionally comprise means for the measurement of other laboratory or clinical parameters. Procedures using these kits may be performed by clinical laboratories, experimental laboratories, medical practitioners, or private individuals.

The kit may additionally comprise one or more other reagents or instruments which enable the method to be carried out. Such reagents or instruments may include one or more of the following: suitable buffer(s) (aqueous solutions), isotopically-labelled or unlabelled peptides, peptide calibration curve standards, developing reagents, enzymes, labels, reacting surfaces, means for detection, control samples, standards, instructions, interpretive information, means to isolate a relevant biomarker from a sample, means to obtain a sample from the individual (such as a vessel or an instrument comprising a needle) or a support comprising wells on which quantitative reactions can be done.

Further Biomarkers Identified According to the Invention

As described in the Examples, in addition to the preferred biomarkers described above initially identified by 2D-PAGE and mass spectrometry and then characterised in more detail for expression in NAFLD (apolipoprotein F, kininogen-1, apolipoprotein D, apolipoprotein M, ficolin-2, alpha-1-acid glycoprotein 2, leucine-rich alpha-2-glycoprotein, lipopolysaccharide-binding protein, thrombospondin-1, IgG Fc-binding protein and cystatin-c), the invention also provides further biomarkers for NAFLD initially identified by 2D-PAGE and mass spectrometry. These further biomarkers are listed below.

The invention thus also provides a method of diagnosing, prognosing or monitoring or staging the progression of non-alcoholic fatty liver disease (NAFLD) in an individual based on detecting and quantitating one or more of the below further biomarkers in a biological sample obtained from the individual, thereby, diagnosing, prognosing or monitoring or staging the progression of NAFLD. The invention additionally provides a method of diagnosing, prognosing or monitoring or staging the progression of non-alcoholic fatty liver disease (NAFLD) in an individual, the method comprising detecting and quantifying one or more biomarkers in a biological sample obtained from the individual, wherein the one or more biomarkers is selected from apolipoprotein F, lipopolysaccharide-binding protein, ficolin-2, apolipoprotein D, kininogen-1, apolipoprotein M, thrombospondin-1, IgG Fc-binding protein, cystatin-c, alpha-1-acid glycoprotein 2, and leucine-rich alpha-2-glycoprotein, and additionally detecting and quantifying one or more of the below further markers, thereby, diagnosing, prognosing or monitoring or staging the progression of NAFLD.

Using 2D-PAGE the following further biomarkers for NAFLD were identified in addition to preferred biomarkers apolipoprotein F, kininogen-1, apolipoprotein D and apolipoprotein M: Proteins identified in features increasing with NAFLD severity included antithrombin-III, alpha-1-antitrypsin, Ig gamma-1 chain C region, complement factor B, alpha-2-macroglobulin, complement factor H, complement C1r subcomponent, complement C4-A, inter-alpha-trypsin inhibitor heavy chain H4, apolipoprotein A-IV and serum albumin. Proteins identified in features decreasing with NAFLD severity included apolipoprotein C2, apolipoprotein C4, apolipoprotein M, apolipoprotein apolipoprotein A-IV, clusterin, protein APOC4-APOC2, haptoglobin, serum albumin, zinc-alpha-2-glycoprotein, thrombin light chain, transthyretin, glutathione peroxidase 3, alpha-1-antitrypsin, alpha-1-antichymotrypsin, LMW kininogen-1, complement C3, complement C4-A, C4b-binding protein alpha chain, complement factor I light chain, complement C1r subcomponent, Ig alpha-1 chain C region, Ig kappa chain C region, Ig gamma-1 chain C region, Ig gamma-2 chain C region, inter-alpha-trypsin inhibitor heavy chain H3, prothrombin, putative elongation factor 1-alpha-like 3, vitamin D-binding protein, beta-2-glycoprotein 1 and alpha-2-HS-glycoprotein.

Three protein features were found to increase in intensity from NAFL to NASH F0/F1 and then decrease in intensity in NASH F3 and the proteins identified in these features included complement C1s subcomponent, complement C3, haptoglobin, apolipoprotein A-IV, serum albumin, Ig kappa chain C region and apolipoprotein A-I. Some proteins were identified in features that were both increasing and decreasing in NAFLD which could be due to post-translational modification or differential expression of different fragments of the protein and these proteins included alpha-1-antitrypsin, Ig gamma-1 chain C region, complement C1r subcomponent, complement C4-A, apolipoprotein A-IV and serum albumin.

Using mass spectrometry and TMT the following further biomarkers for NAFLD were identified in addition to preferred biomarkers ficolin-2, alpha-1-acid glycoprotein 2, leucine-rich alpha-2-glycoprotein, lipopolysaccharide-binding protein, thrombospondin-1, IgG Fc-binding protein and cystatin-c: Proteins identified to be increasing with NAFLD severity included Cystatin-C (P01034), Phosphatidylinositol-glycan-specific phospholipase D (P80108), GTPase-activating Rap/Ran-GAP domain-like protein 3 (Q5VVW2), Ig kappa chain V-I region DEE (P01597), Ficolin-3 (O75636), Alpha-2-HS-glycoprotein (P02765), Hepatocyte growth factor-like protein (P26927), Carbonic anhydrase 1 (P00915), Ig heavy chain V-II region WAH (P01824), Ig kappa chain V-I region Mev (P01612), Properdin (P27918), Ig kappa chain V-III region HAH (P18135), Hemoglobin subunit beta (P68871), von Willebrand factor (P04275), Hemoglobin subunit alpha (P69905), Ig kappa chain V-I region Ni (P01613), Ig kappa chain V-I region EU (P01598), Ig alpha-1 chain C region (P01876), SPARC (P09486), Fibronectin (P02751), Platelet basic protein (P02775) and Platelet factor 4 (P02776). Proteins identified to be decreasing with NAFLD severity included Pregnancy zone protein (P20742), Apolipoprotein (a) (P08519), Coagulation factor XIII A chain (P00488), Galectin-3-binding protein (Q08380), Adiponectin (Q15848), Actin cytoplasmic 1 (P60709), Apolipoprotein A-II (P02652), Alpha-2-antiplasmin (P08697), Peptidase inhibitor 16 (Q6UXB8), Zinc-alpha-2-glycoprotein (P25311), Alpha-1-acid glycoprotein 2 (P19652), Coagulation factor XI (P03951), Serum amyloid P-component (P02743), Protein Z-dependent protease inhibitor (Q9UK55), Monocyte differentiation antigen CD14 (P08571), Insulin-like growth factor-binding protein complex acid labile subunit (P35858) and Apolipoprotein L1 (O14791).

One or more of the following biomarkers may also be analysed in addition to the biomarkers/biomarker combinations of the invention in the methods provided herein: afamin, alanine aminotransferase (ALT), alpha-1B-glycoprotein, alpha-1-microglobulin, alphafetoprotein (AFP), angiotensin 2, angiotensinogen, apolipoprotein A-1, apolipoprotein C1, apolipoprotein C2, apolipoprotein E, asialoglycoprotein receptor 1, asialoglycoprotein receptor 2, aspartate aminotransferase (AST), beta 2 microglobulin, bilirubin, biotinidase, blood cholesterol, blood glucose (fasting and/or postprandial), blood triglycerides, blood urea nitrogen (BUN), bradykinin, C-reactive protein (CRP), carboxypeptidase N2, C4b-binding protein beta chain, CD5 antigen like protein (CDSL), ceruloplasmin, chitinase-3-like protein 1, collagenpeptidase, complement C3 (including C3dg and its cleavage at the thioester site between amino acids 1010-1013), complement factor H-related protein 1, connective tissue growth factor, collagen IV, collagen VI, collagen XIV, 72 kDa type IV collagenase, corticosteroid-binding globulin, creatinine, dickkopf-1, epithelial cell adhesion molecule, fibrinogen gamma chain, fibronectin type III domain-containing protein 5, ficolin-1, full blood count, galactosylhydroxylysyl-glucosyltransferase, gamma-glutamyl transpeptidase, gelatinase B, gelsolin, glypican-3, golgi membrane protein 1, haptoglobin (including the beta chain at pH 5.46-5.49 with glycans which are mainly biantennary, both mono- or disialylated with hardly any tri- or tetra-antennary/sialylated structures and less sialic acid and more monosialylated structures than the other haptoglobin isoforms of lower pH), haptoglobin-related protein, hemoglobin A1c, hemopexin, high density lipoprotein (HDL), hyaluronic acid, immunoglobulin J chain, inter-alpha-trypsin inhibitor (H1, H2, H5, H6), intracellular adhesion molecule 1, irisin, laminin subunit alpha/beta/gamma (including laminin P1-fragment), lecithin cholesterol acyltransferase, liver function tests, low density lipoprotein (LDL), lysylhydroxylase, lysyloxidase, matrix metalloproteinases (MMP-1 to MMP-28), metalloproteinase inhibitors (TIMP1, TIMP2, TIMP3, TIMP4), microfibril-associated protein 4, monoamine-oxidase, N-Acetyl-beta-d-glucosaminidase, osteopontin, peroxiredoxin-2, phosphatidylcholine-sterol acyltransferase, pigment epithelium-derived factor, platelet count, platelet-derived growth factor, procollagen type I (including N-terminal propeptide and C-terminal propeptide), procollagen type III (including intact procollagen, N-terminal propeptide, C-terminal propeptide, complete propeptide Col 1-3), globular domain of propeptide Col-1), prolylhydroxylase, 14-3-3 protein zeta/delta, protein AMBP, prothrombin (index/prothrombin time/INR ratio), resistin, retinol-binding protein 4, sal-like protein 4, serum paraoxonase/arylesterase 1, sex hormone-binding globulin, SNC73, talin-1, tenascin, thrombospondin-2, thrombospondin-3, thrombospondin-4, thrombospondin-5, transferrin, transforming growth factor alpha (TGF alpha), transforming growth factor beta-1 (TGF beta-1), tropomyosin (1-4), tumor necrosis factor (TNF alpha), type IV collagen (including NC1-fragment C-terminal crosslinking domain PIVP and 7S domain/7S collagen), type VI collagen, undulin, vascular cell adhesion molecule and/or vitronectin.

EXAMPLES

Differentially Expressed Proteins Established When Comparing Plasma From Patients With Different Stages of NAFLD The inventors have discovered that various proteins are differentially expressed in human serum samples of NAFLD patients. The following groups were compared: NAFL, NASH with no fibrosis F0, NASH with mild fibrosis F1 and NASH with advanced fibrosis F3. This discovery was achieved by comparing these serum samples using two proteomics methods: Two dimensional polyacrylamide gel electrophoresis (2D-PAGE) and TMT-based mass spectrometry.

Example 1

Two Dimensional Polyacrylamide Gel Electrophoresis (2D-PAGE)

To identify biomarkers for NAFLD, serum samples were analyzed using two 2D-PAGE-based proteomics approaches. The following NAFLD stages were analyzed: NAFL, NASH with no fibrosis F0, NASH with mild fibrosis F1 and NASH with advanced fibrosis F3.

In the first approach, twelve highly abundant serum proteins were depleted from all NAFLD samples by immunoprecipitation using the Top 12 Abundant Protein Depletion Spin Column (Thermo Scientific, Loughborough, UK) according to the manufacturer's protocol. The 12 proteins which were depleted were alpha 1-acid glycoprotein, alpha 1-antitrypsin, alpha 2-macroglobin, albumin, apolipoprotein A-I, apolipoprotein A-II, fibrinogen, haptoglobin, IgA, IgG, IgM and transferrin. Fifty micrograms of the depleted serum proteins were separated by charge using a 7 cm pH 3-11 non-linear gradient in the first dimension of the gel followed by molecular weight (size) in the second dimension using a 4-12% (w/v) SDS-PAGE gradient. Electrophoresis, fluorescent staining and scanning of gels were performed as described by Gangadharan et al., (2007), Clin Chem, 53, 1792.

In the second approach, two milligrams of undepleted serum proteins were separated by charge using a pH 3-5.6 non-linear gradient in the first dimension o followed by molecular weight in the second dimension using a 9-16% (w/v) SDS-PAGE gradient. Electrophoresis, fluorescent staining and scanning of gels were performed as described by Gangadharan et al., (2012), PLoS ONE, 7, e39603; Gangadharan et al., (2011), Nature Protocol Exchange, doi:10.1038/protex.2011.261 and Gangadharan et al., (2011), J Proteome Res, 10, 2643.

Example 2

Differential Image Analysis and Protein Identification

The two dimensional array of spots generated were compared among the different NAFLD stages by computer-aided image analysis. Scanned images of all 2D-PAGE gels were analyzed by computer-aided image analysis using the Progenesis SameSpots software (Nonlinear Dynamics Limited, Newcastle, UK). Images were processed in an automated linear workflow, including gel alignment, spot detection, spot splitting and statistical analysis. Spot detection produced a complete data set as all gels contain the same number of spots, each matched to its corresponding spot on all gels. There were no missing values allowing valid statistical analysis to be applied. Only differentially expressed changes that were 1.5-fold or more different and also had ANOVA p-value≤0.05 for 95% confidence were considered to be statistically significant. All changes shown on the list were visualized and confirmed across all gels. A total of 15 differentially expressed features were observed using the pH 3-11 gels with depleted serum. A total of 38 differentially expressed features were observed using the pH 3-5.6 gels with undepleted serum. Overall 11 proteins were identified in features increasing with NAFLD severity and 35 proteins were identified in features decreasing with NAFLD severity (i.e. a total of 46 proteins). Examples of differentially expressed features are shown in FIG. 1. These differentially expressed features were excised from the gels, the proteins in the gel pieces were digested with trypsin, and the peptides were analyzed by mass spectrometry to identify the biomarkers essentially as described by Gangadharan et al., (2007), Clin. Chem., 53, 1792 and Gangadharan et al., (2012), PLoS ONE, 7, e39603.

Figure 2:
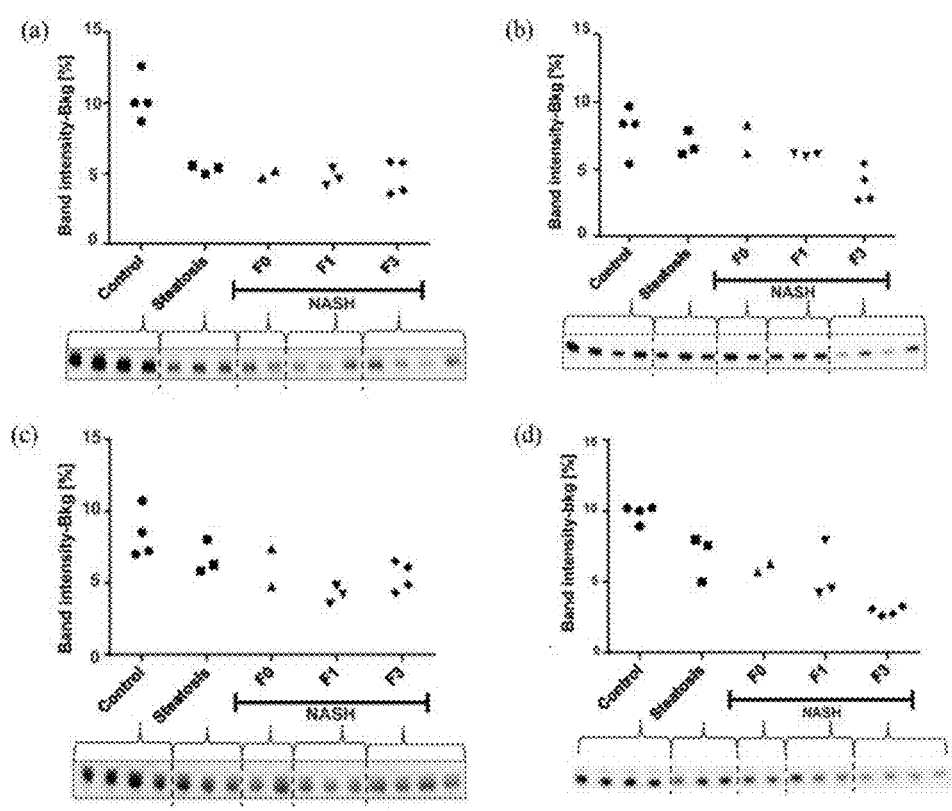
FIG. 2—Western blot densitometry data for novel biomarkers using patient serum samples with increasing NAFLD severity. (a) apolipoprotein D; this biomarker is high in healthy controls and consistently lower in all stages of NAFLD suggesting that it would be useful as an early NAFLD biomarker. (b) apolipoprotein M; the biomarker shows a slight decrease from steatosis (NAFL) to NASH F0 but reduces markedly in expression in NASH F3 suggesting that it is most useful at determining hepatic fibrosis. (c) kininogen-1; a consistent decrease across all NAFLD stages. (d) apolipoprotein F; a consistent decrease across all NAFLD stages.

The proteins in the NAFLD serum samples were separated by SDS-PAGE followed by Western blotting using antibodies against the novel biomarkers. Apolipoprotein F and kininogen-1 were shown to decrease across all NAFLD stages. Apolipoprotein D was higher in healthy controls compared to all stages of NAFLD suggesting that it has the potential to be an early NAFLD marker and capable of differentiating healthy controls from patients with NAFL. Apolipoprotein M levels appeared to be consistent in healthy controls and all NAFLD stages except for NASH F3 suggesting that this is an advanced fibrosis biomarker. The Western blots for these four NAFLD biomarkers are shown in FIG. 2 and these four biomarkers were considered as particularly preferred biomarkers out of the original list of 46 proteins initially identified by 2D-PAGE.

Example 3

TMT-Based Mass Spectrometry

Figure 3:
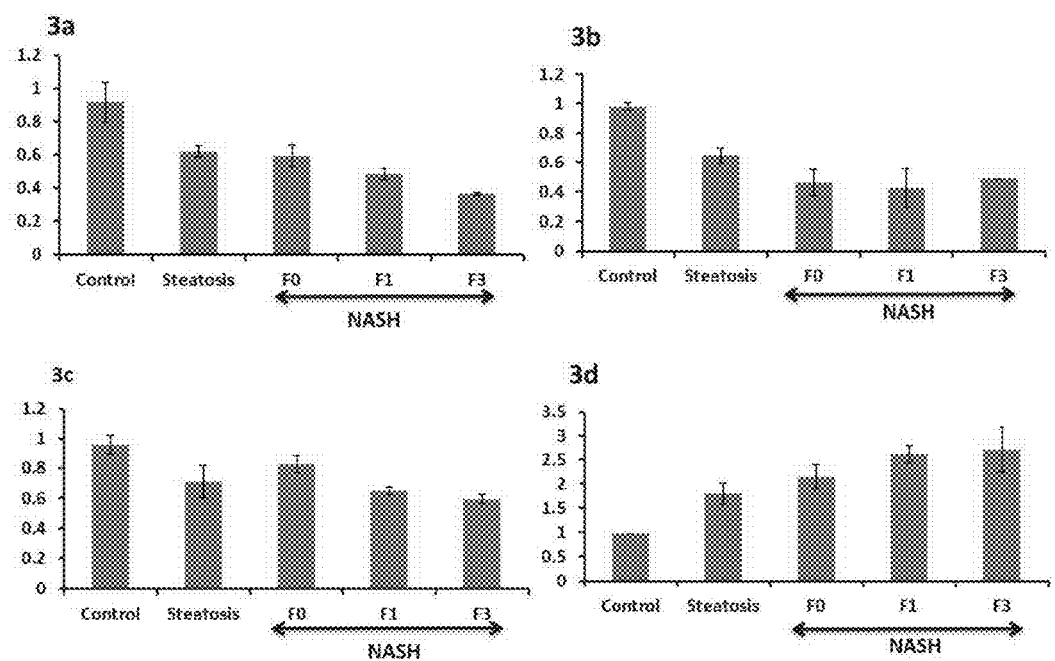
FIG. 3—Mass spectrometric relative quantitation data from the use of tandem mass tags (TMT; 10-plex) for novel NAFLD biomarkers using serum samples from healthy individuals (control) and patients with steatosis (NAFL) and NASH (with Kleiner-Brunt scores of F0, F1 and F3). (3a) Apolipoprotein F (APO-F) shows a decrease in its concentration with increasing NAFLD severity. (3b) Adiponectin decreases in its concentration from control to steatosis (NAFL) to NASH but is constant in all fibrosis stages of NASH suggesting that it is a good NAFLD biomarker. (3c) Ficolin-2 shows some decrease in NAFLD with its lowest levels in fibrosis stage F3. (3d) Thrombospondin-1 increases from control to steatosis (NAFL) and across all stages of NAFLD.

Two serum samples from each of the following five stages were analyzed: 1) healthy individuals, 2) NAFL, 3) NASH with no fibrosis F0, 4) NASH with mild fibrosis F1 and 5) NASH with advanced fibrosis F3. The proteins in these ten samples were digested with trypsin and the tryptic peptides were labelled with an isobaric isotopically labelled tandem mass tag (TMT) according to the manufacturer's protocol (Life Technologies). All ten samples with TMT labelled peptides were mixed and analyzed by LC-MS/MS using the Dionex Ultimate 3000 UHPLC and Thermo Q Exactive hybrid quadrupole-Orbitrap mass spectrometer. Using this method a total of 54 differentially expressed serum proteins were observed. Examples of differentially expressed proteins based on relative quantitation TMT data are shown in FIG. 3.

Figure 4:
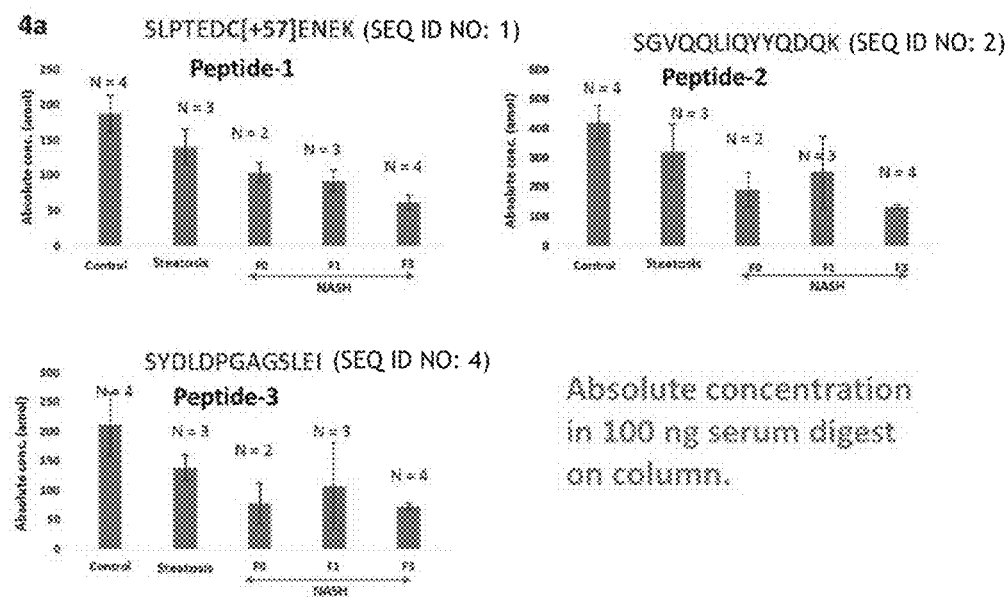
FIG. 4—Parallel reaction monitoring (PRM) based mass spectrometric quantitation data for selected potential biomarkers. (4a) Absolute concentration of APO-F using three different tryptic peptides in its sequence. A digest of the serum samples (100 ng) was used to quantify APO-F using the IGNIS LC-MS method. (4b-i) Relative quantitation of biomarkers using PRM for (4b) ficolin-2, (4c) thrombospondin-1, (4d) adiponectin, (4e) IgG Fc-binding protein, (4f) cystatin-C, (4g) lipopolysaccharide-binding protein, (4h) alpha-1-acid glycoprotein 2, (4i) leucine-rich alpha-2-glycoprotein and (4j) apolipoprotein D. All the samples were analyzed in two technical replicates.
Figure 4:
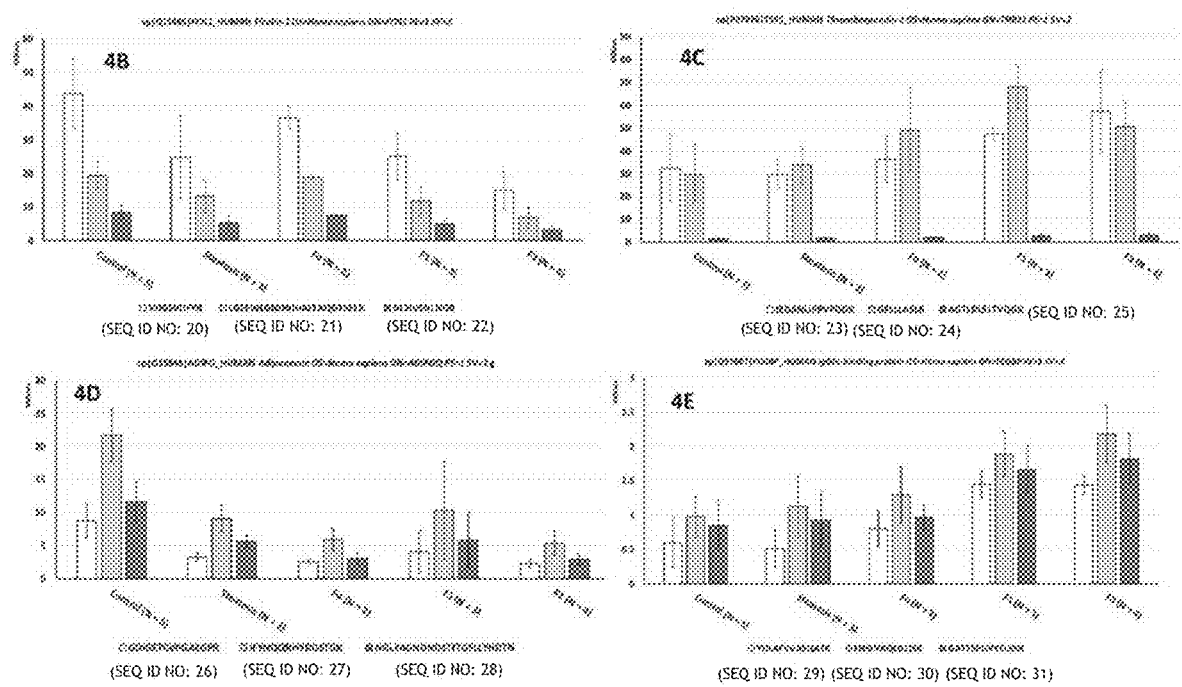
Figure 4:
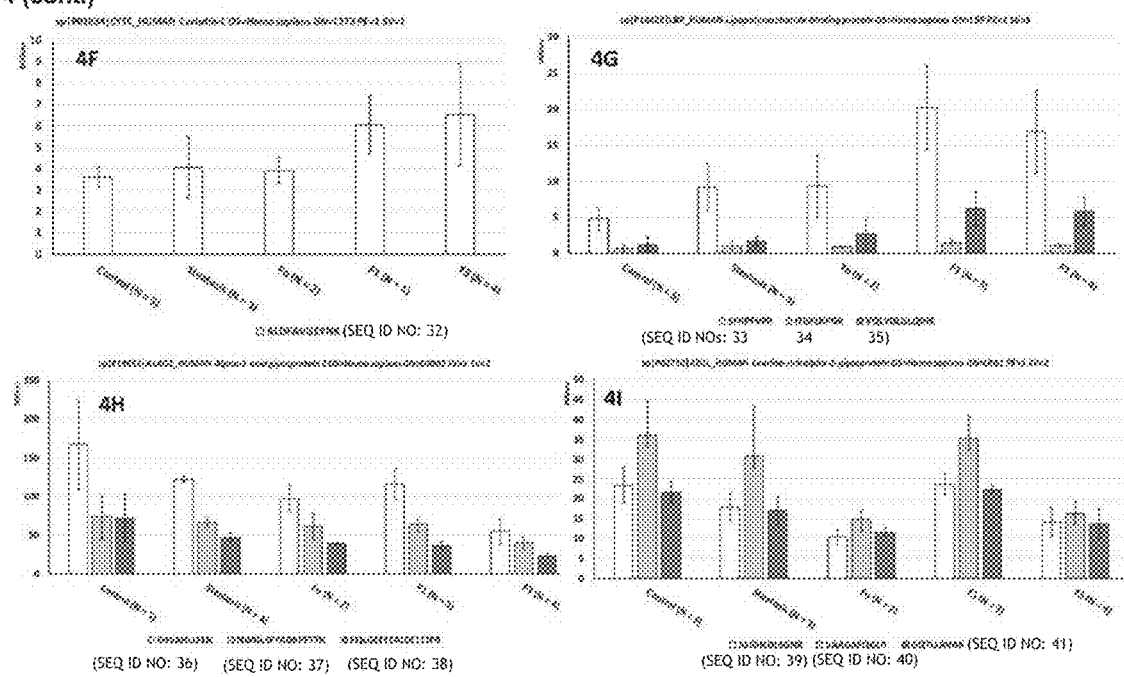
Figure 4:
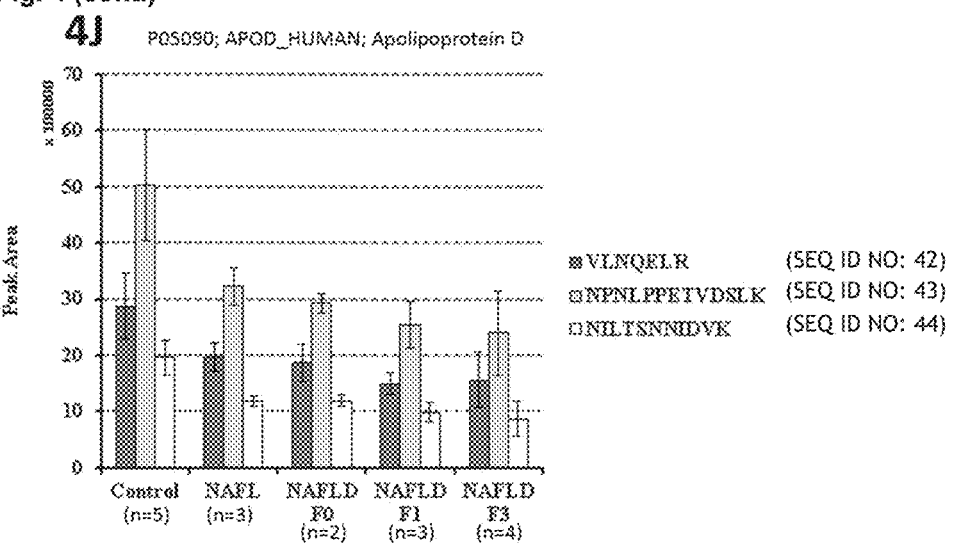

All 54 differentially expressed proteins were targeted by PRM, with three peptides for each protein wherever possible, using tryptic digests of the serum samples. This validation check helped to identify which of the 54 potential NAFLD biomarkers were the most promising. Of the 54 proteins, 8 proteins not previously identified in Example 2 were found to be particularly promising biomarkers (thus giving a total of 12 particularly promising biomarkers including the 4 listed in Example 2). From the list of 8 proteins, ficolin-2, adiponectin, alpha-1-acid glycoprotein 2 and leucine-rich alpha-2-glycoprotein all showed a decrease across NAFLD stages whereas lipopolysaccharide-binding protein, thrombospondin-1, IgG Fc-binding protein and cystatin-c showed an increase across NAFLD stages. The PRM data for these 8 NAFLD biomarkers along with apolipoprotein D are shown in FIG. 4.

Example 4

NAFLD and/or Fibrosis Scoring Scale

A NAFLD and/or fibrosis scoring scale for each of the novel biomarkers can be formulated. The average concentration of these biomarkers in capillary blood, venous blood, arterial blood, serum, plasma or other bodily fluid over the various stages of NAFLD and/or liver fibrosis is determined. In NAFLD, the Kleiner-Brunt scale of 0 to 4 is presently used to assess liver fibrosis in the clinic where 0 represents no fibrosis, 1-3 represent the intermediate stages of fibrosis in increasing severity from mild to moderate/severe and 4 is cirrhosis (Kleiner, (2005), Hepatology, 41, 1313). Fibrosis can also be stages on other similar scales from 0 to 4 (such as Metavir, Knodell) or 0 to 6 where 0 represents no fibrosis, 1-5 represent the intermediate stages of fibrosis in increasing severity from mild to moderate/severe and 6 is cirrhosis (Ishak, (1995), J Hepatol, 22, 696). By determining the concentration ranges of the novel biomarkers across these stages, a similar mathematical scoring algorithm as in Kleiner-Brunt or similar can be assigned to help provide information on staging and prognosis. The additive results from the scores of more than one of the novel biomarkers may give a more reliable indication of the degree of fibrosis rather than examining individual biomarkers. The scoring method may not necessarily follow existing scores such as Kleiner-Brunt, Ishak, Metavir, Knodell or the like and may be a novel scoring scale to help determine NAFLD and/or fibrosis stage and to determine if treatment is necessary.

Example 5

Quantitation by Mass Spectrometry

An antibody-free approach using mass spectrometry may be used to determine NAFLD and/or fibrosis stage by detecting and/or quantifying one or more biomarkers of interest. The proteins in the biological sample (either capillary blood, venous blood, arterial blood, serum, plasma or other bodily fluid) are usually denatured with urea or the like. Proteins can optionally be reduced (using dithiothreitol, tris(2-carboxyethyl)phosphine, beta mercaptoethanol or the like) and alkylated (using iodoacetamide or the like) and these steps are usually carried out prior to digestion although they can be carried out post digestion. Proteins are digested with an enzyme such as trypsin, chymotrypsin or the like. In the case of trypsin, this also includes immobilized trypsin for higher throughput digestion such as Flash digest from Perfinity Biosciences (also called SMART Digest from Thermo Scientific). Protein digestion can be carried out using in-solution digestion, Filter Aided Sample Preparation (FASP), in-gel digestion (where the sample is either run into an SDS-PAGE gel, optionally stained and excised for digestion or is cast in a gel block of polyacrylamide before digestion), immobilized enzyme digestion (such as Flash Digest from Perfinity Biosciences or SMART Digest from Thermo Fisher Scientific) or the like. Isotopically labeled peptide standards can be spiked into the biological sample either before or after digestion and these include synthetic peptides, IGNIS peptides, PEPotec peptides, AQUA peptides, SpikeTide peptides, Protein Epitope Signature Tag (QPrEST) peptides, microwave-assisted solid phase synthesized peptides, concatenated signature peptides encoded by QconCAT genes or the like.

The protein cleavage sites for different enzymes such as trypsin are known and so the biomarkers are digested in-silico either manually or using a software (such as Skyline, PinPoint or the like) to help determine suitable peptides for targeted quantitation. Typically peptides selected are longer than 7 amino acids, shorter than 25 amino acids, not modified (such as glycosylation, phosphorylation or the like) and not containing a methionine although peptides outside this criteria should not be entirely excluded. Online databases such as, but not limited to, PeptideAtlas and the Global Proteome Machine database (gpmdb), help to determine the commonly observed peptides for the proteins of interest. MRMaid can be used to help design assays for mass spectrometry based targeted quantitation by suggesting peptides and MS2 ions to monitor based on experimental spectra from the PRIDE database. Protein BLAST is used to check the uniqueness of the selected peptide. If a peptide is found to be not unique, then another peptide within the biomarker sequence would be selected.

Prior to mass spectrometry, digested peptides can be fractionated using phosphopeptide enrichment, glycopeptide enrichment, high pH reversed phase fractionation or the like. Peptides can be separated by reversed phase liquid chromatography, hydrophilic interaction liquid chromatography (HILIC), ion-exchange chromatography, isoelectric focusing or the like.

SRM/MRM is performed using a triple quadrupole mass spectrometer which has three quadrupoles which include instruments such as the Thermo TSQ Quantiva, Waters Xevo TQ-S, Agilent 6495, Bruker EVOQ, ABSciex 3500, Shimadzu 8050 or the like. PRM is performed using a hybrid quadrupole-Orbitrap mass spectrometer such as a Thermo Q Exactive and its variants or a Thermo Fusion and its variants. MRM3 is performed using a QTRAP mass spectrometer such as the ABSciex QTRAP 6500. The area under the curve (AUC) of the fragment ions can be used to relatively quantify the levels of the proteins of interest. Known amounts of synthetic pure heavy-labelled peptides, such as AQUA peptides or the like, with the same sequence as the preselected peptides can be used to establish a calibration curve to help determine the absolute concentration of the proteins. Alternatively absolute quantitation can be carried out using the HeavyPeptide IGNIS Prime Custom Peptide Quantitation Kit from Life Technologies.

The inventors also propose that any biomarkers which cleave or have a region of interest could be targeted by mass spectrometry using peptide standards covering these cleavage regions or regions of interest to be used in a mass spectrometry assay.

Example 6

Immunoassay

An immunoassay may be performed to assess the levels of biomarker such as enzyme linked immunosorbent assay (ELISA), radio-immunoassay, protein dot blot, Western blot, turbidimetry, nephelometry and the like.

In the cases of an ELISA, the assay can be performed in a 96-well plate. One option is to use the non-competitive one-site binding ELISA. In this assay, capillary blood, venous blood, arterial blood, serum, plasma or other bodily fluid along with known concentrations of antigen are prepared in a buffer such as a bicarbonate buffer, added to the 96-well plate and incubated over a set period such as overnight at 4° C. The wells are then washed with a solution such as phosphate buffered saline (PBS) and Tween (PBS-T) or the like followed by blocking with a PBS solution containing bovine serum albumin or the like. After an incubation period (such as 37° C. for 1 hour), a primary antibody directed against the antigen (in this example, the biomarker of interest) is added, the plate incubated for a period (such as 37° C. for 1 hour) and then washed with PBS-T or the like. A conjugated secondary antibody (such as horseradish peroxidase), directed against the animal origin of the primary antibody, is then added, and the plate incubated for a period (such as 37° C. for 1 hour) followed by washes with PBS-T or the like. Finally, a substrate (e.g. a peroxidase substrate such as 2,2'-azino-bis(3-ethylbenzthiazoline-6-sulphonic acid, ABTS) is added to each well and the absorbance read on a plate reader (e.g. at 405 nm after 30 minutes for ABTS).

Alternatively, a sandwich ELISA can be used. In this type of assay, one antibody is bound to the bottom of a plate well. The antigen, in this case the biomarker protein, is added and unbound products are removed by washing. A second, labeled antibody that binds to the antigen is then added. The amount of bound secondary antibody is quantified, usually colorimetrically. In addition to the novel biomarkers, the inventors propose that any biomarkers which cleave or have a region of interest, then antibodies could be raised which target these cleavage regions or regions of interest to be used in an immunoassay.

The invention claimed is:

1. A method of treating non-alcoholic fatty liver, the method comprising:
   diagnosing non-alcoholic fatty liver in an individual, by a method comprising diagnosing, prognosing or monitoring or staging progression of non-alcoholic fatty liver in the individual, the method comprising:
   detecting and quantifying thrombospondin-1 in a biological sample obtained from the individual;
   comparing the level of thrombospondin-1 in the biological sample obtained from the individual to the level of thrombospondin-1 in a control group of healthy individuals and determining whether the level of thrombospondin-1 in the biological sample obtained from the individual is indicative of progression of non-alcoholic fatty liver, wherein an increasing level of thrombospondin-1, as compared with the control group, indicates increasing severity of non-alcoholic fatty liver in the individual,
   and thereby diagnosing, prognosing or monitoring or staging the progression of non-alcoholic fatty liver in the individual; and wherein the method further comprises:
   administering an agent or carrying out a regimen to reduce or prevent the development or progression of non-alcoholic fatty liver or effective to treat non-alcoholic fatty liver to the individual.

2. The method of claim 1, wherein the method comprises detecting and quantifying one or more peptides derived from thrombospondin-1, wherein the one or more peptides are selected from:
   IEDANLIPPVPDDK (SEQ ID NO: 23), GFLLLASLR (SEQ ID NO: 24) and/or AGTLDLSLTVQGK (SEQ ID NO: 25).

3. The method of claim 1, comprising detecting and quantifying thrombospondin-1, and one or more, two or more, three or more or four or more biomarkers selected from the group consisting of lipopolysaccharide-binding protein, apolipoprotein F, ficolin-2, apolipoprotein D, kininogen-1, apolipoprotein M, IgG Fc-binding protein, cystatin-c, alpha-1-acid glycoprotein 2, and leucine-rich alpha-2-glycoprotein.

4. The method of claim 1, further comprising detecting and quantifying one or more biomarkers selected from the group consisting of apolipoprotein F, lipopolysaccharide-binding protein, ficolin-2, and apolipoprotein D.

5. The method of claim 4, further comprising detecting and quantifying alpha-1-acid glycoprotein 2.

6. The method of claim 1, further comprising detecting and quantifying:
   (i) the biomarker adiponectin;
   (ii) the biomarker keratin type I cytoskeletal 18 and optionally its cleavage between amino acids 397/398; and/or
   (iii) cleavage products of a protein, selected from kininogen-1, keratin type I cytoskeletal 18 and angiotensinogen.

7. The method of claim 1, wherein the biological sample is blood, serum or plasma.

8. The method of claim 1, wherein the individual is already diagnosed with NAFLD.

9. The method of claim 1, wherein the sample is analysed using a mass spectrometry method.

10. The method of claim 9, wherein the mass spectrometry method is Parallel-Reaction Monitoring (PRM), Selected Reaction Monitoring (SRM), Multiple Reaction Monitoring (MRM), or multi-stage fragmentation in MRM-cubed (MRM3).

11. The method of claim 1, wherein the sample is analysed using an immunoassay.

12. The method of claim 11, wherein the immunoassay is ELISA, a radioimmunoassay, dot blot, Western blot, turbidimetry or nephelometry.

* * * * *

SEQUENCE LISTING

<160> NUMBER OF SEQ ID NOS: 44

<210> SEQ ID NO 1
<211> LENGTH: 11
<212> TYPE: PRT
<213> ORGANISM: Artificial Sequence
<220> FEATURE:
<223> OTHER INFORMATION: APO-F peptide-1

<400> SEQUENCE: 1

Ser Leu Pro Thr Glu Asp Cys Glu Asn Glu Lys
1               5                   10

<210> SEQ ID NO 2
<211> LENGTH: 14
<212> TYPE: PRT
<213> ORGANISM: Artificial Sequence
<220> FEATURE:
<223> OTHER INFORMATION: APO-F peptide-2

<400> SEQUENCE: 2

Ser Gly Val Gln Gln Leu Ile Gln Tyr Tyr Gln Asp Gln Lys
1               5                   10

<210> SEQ ID NO 3
<211> LENGTH: 11

```
<212> TYPE: PRT
<213> ORGANISM: Artificial Sequence
<220> FEATURE:
<223> OTHER INFORMATION: APO-F peptide-4
<220> FEATURE:
<221> NAME/KEY: MOD_RES
<222> LOCATION: (10)..(10)
<223> OTHER INFORMATION: may be O-glycosylated threonine

<400> SEQUENCE: 3

Asp Ala Asn Ile Ser Gln Pro Glu Thr Thr Lys
1               5                   10

<210> SEQ ID NO 4
<211> LENGTH: 13
<212> TYPE: PRT
<213> ORGANISM: Artificial Sequence
<220> FEATURE:
<223> OTHER INFORMATION: APO-F peptide-3

<400> SEQUENCE: 4

Ser Tyr Asp Leu Asp Pro Gly Ala Gly Ser Leu Glu Ile
1               5                   10

<210> SEQ ID NO 5
<211> LENGTH: 25
<212> TYPE: PRT
<213> ORGANISM: Artificial Sequence
<220> FEATURE:
<223> OTHER INFORMATION: tryptic peptide 1 of keratin type 1
      cytoskeletal 18

<400> SEQUENCE: 5

Leu Leu Glu Asp Gly Glu Asp Phe Asn Leu Gly Asp Ala Leu Asp Ser
1               5                   10                  15

Ser Asn Ser Met Gln Thr Ile Gln Lys
            20                  25

<210> SEQ ID NO 6
<211> LENGTH: 15
<212> TYPE: PRT
<213> ORGANISM: Artificial Sequence
<220> FEATURE:
<223> OTHER INFORMATION: cleaved tryptic peptide 1 of keratin type 1
      cytoskeletal 18

<400> SEQUENCE: 6

Leu Leu Glu Asp Gly Glu Asp Phe Asn Leu Gly Asp Ala Leu Asp
1               5                   10                  15

<210> SEQ ID NO 7
<211> LENGTH: 10
<212> TYPE: PRT
<213> ORGANISM: Artificial Sequence
<220> FEATURE:
<223> OTHER INFORMATION: cleaved tryptic peptide 2 of keratin type 1
      cytoskeletal 18

<400> SEQUENCE: 7

Ser Ser Asn Ser Met Gln Thr Ile Gln Lys
1               5                   10

<210> SEQ ID NO 8
<211> LENGTH: 14
<212> TYPE: PRT
<213> ORGANISM: Artificial Sequence
<220> FEATURE:
<223> OTHER INFORMATION: T-kinin
```

```
<400> SEQUENCE: 8

Ile Ser Leu Met Lys Arg Pro Pro Gly Phe Ser Pro Phe Arg
1               5                   10

<210> SEQ ID NO 9
<211> LENGTH: 9
<212> TYPE: PRT
<213> ORGANISM: Artificial Sequence
<220> FEATURE:
<223> OTHER INFORMATION: bradykinin
<220> FEATURE:
<221> NAME/KEY: MOD_RES
<222> LOCATION: (3)..(3)
<223> OTHER INFORMATION: maybe Hydroxylated proline

<400> SEQUENCE: 9

Arg Pro Pro Gly Phe Ser Pro Phe Arg
1               5

<210> SEQ ID NO 10
<211> LENGTH: 10
<212> TYPE: PRT
<213> ORGANISM: Artificial Sequence
<220> FEATURE:
<223> OTHER INFORMATION: lysyl-bradykinin

<400> SEQUENCE: 10

Lys Arg Pro Pro Gly Phe Ser Pro Phe Arg
1               5                   10

<210> SEQ ID NO 11
<211> LENGTH: 8
<212> TYPE: PRT
<213> ORGANISM: Artificial Sequence
<220> FEATURE:
<223> OTHER INFORMATION: glycated N terminal peptide from hemoglobin
      beta chain
<220> FEATURE:
<221> NAME/KEY: MOD_RES
<222> LOCATION: (1)..(1)
<223> OTHER INFORMATION: may be glycated valine

<400> SEQUENCE: 11

Val His Leu Thr Pro Glu Glu Lys
1               5

<210> SEQ ID NO 12
<211> LENGTH: 10
<212> TYPE: PRT
<213> ORGANISM: Artificial Sequence
<220> FEATURE:
<223> OTHER INFORMATION: angiotensin-1

<400> SEQUENCE: 12

Asp Arg Val Tyr Ile His Pro Phe His Leu
1               5                   10

<210> SEQ ID NO 13
<211> LENGTH: 9
<212> TYPE: PRT
<213> ORGANISM: Artificial Sequence
<220> FEATURE:
<223> OTHER INFORMATION: angiotensin 1-9

<400> SEQUENCE: 13

Asp Arg Val Tyr Ile His Pro Phe His
1               5
```

```
<210> SEQ ID NO 14
<211> LENGTH: 8
<212> TYPE: PRT
<213> ORGANISM: Artificial Sequence
<220> FEATURE:
<223> OTHER INFORMATION: angiotensin-2

<400> SEQUENCE: 14

Asp Arg Val Tyr Ile His Pro Phe
1               5

<210> SEQ ID NO 15
<211> LENGTH: 7
<212> TYPE: PRT
<213> ORGANISM: Artificial Sequence
<220> FEATURE:
<223> OTHER INFORMATION: angiotensin 1-7

<400> SEQUENCE: 15

Asp Arg Val Tyr Ile His Pro
1               5

<210> SEQ ID NO 16
<211> LENGTH: 5
<212> TYPE: PRT
<213> ORGANISM: Artificial Sequence
<220> FEATURE:
<223> OTHER INFORMATION: angiotensin 1-5

<400> SEQUENCE: 16

Asp Arg Val Tyr Ile
1               5

<210> SEQ ID NO 17
<211> LENGTH: 4
<212> TYPE: PRT
<213> ORGANISM: Artificial Sequence
<220> FEATURE:
<223> OTHER INFORMATION: angiotensin 1-4

<400> SEQUENCE: 17

Asp Arg Val Tyr
1

<210> SEQ ID NO 18
<211> LENGTH: 7
<212> TYPE: PRT
<213> ORGANISM: Artificial Sequence
<220> FEATURE:
<223> OTHER INFORMATION: angiotensin-3

<400> SEQUENCE: 18

Arg Val Tyr Ile His Pro Phe
1               5

<210> SEQ ID NO 19
<211> LENGTH: 6
<212> TYPE: PRT
<213> ORGANISM: Artificial Sequence
<220> FEATURE:
<223> OTHER INFORMATION: angiotensin-4

<400> SEQUENCE: 19

Val Tyr Ile His Pro Phe
1               5
```

```
<210> SEQ ID NO 20
<211> LENGTH: 9
<212> TYPE: PRT
<213> ORGANISM: Artificial Sequence
<220> FEATURE:
<223> OTHER INFORMATION: Ficolin-2 peptide-1

<400> SEQUENCE: 20

Val Asp Gly Ser Val Asp Phe Tyr Arg
1               5

<210> SEQ ID NO 21
<211> LENGTH: 23
<212> TYPE: PRT
<213> ORGANISM: Artificial Sequence
<220> FEATURE:
<223> OTHER INFORMATION: Ficolin-2 peptide-2

<400> SEQUENCE: 21

Leu Gly Glu Phe Trp Leu Gly Asn Asp Asn Ile His Ala Leu Thr Ala
1               5                   10                  15

Gln Gly Thr Ser Glu Leu Arg
            20

<210> SEQ ID NO 22
<211> LENGTH: 10
<212> TYPE: PRT
<213> ORGANISM: Artificial Sequence
<220> FEATURE:
<223> OTHER INFORMATION: Ficolin-2 peptide-3

<400> SEQUENCE: 22

Asn Cys His Val Ser Asn Leu Asn Gly Arg
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Thrombospondin-1 peptide-1

<400> SEQUENCE: 23

Ile Glu Asp Ala Asn Leu Ile Pro Pro Val Pro Asp Asp Lys
1               5                   10

<210> SEQ ID NO 24
<211> LENGTH: 9
<212> TYPE: PRT
<213> ORGANISM: Artificial Sequence
<220> FEATURE:
<223> OTHER INFORMATION: Thrombospondin-1 peptide-2

<400> SEQUENCE: 24

Gly Phe Leu Leu Leu Ala Ser Leu Arg
1               5

<210> SEQ ID NO 25
<211> LENGTH: 13
<212> TYPE: PRT
<213> ORGANISM: Artificial Sequence
<220> FEATURE:
<223> OTHER INFORMATION: Thrombospondin-1 peptide-3

<400> SEQUENCE: 25

Ala Gly Thr Leu Asp Leu Ser Leu Thr Val Gln Gly Lys
```

<210> SEQ ID NO 26
<211> LENGTH: 15
<212> TYPE: PRT
<213> ORGANISM: Artificial Sequence
<220> FEATURE:
<223> OTHER INFORMATION: Adiponectin peptide-1

<400> SEQUENCE: 26

Gly Asp Ile Gly Glu Thr Gly Val Pro Gly Ala Glu Gly Pro Arg
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Adiponectin peptide-2

<400> SEQUENCE: 27

Ile Phe Tyr Asn Gln Gln Asn His Tyr Asp Gly Ser Thr Gly Lys
1               5                   10                  15

<210> SEQ ID NO 28
<211> LENGTH: 23
<212> TYPE: PRT
<213> ORGANISM: Artificial Sequence
<220> FEATURE:
<223> OTHER INFORMATION: Adiponectin peptide-3

<400> SEQUENCE: 28

Asn Gly Leu Tyr Ala Asp Asn Asp Asn Asp Ser Thr Phe Thr Gly Phe
1               5                   10                  15

Leu Leu Tyr His Asp Thr Asn
            20

<210> SEQ ID NO 29
<211> LENGTH: 13
<212> TYPE: PRT
<213> ORGANISM: Artificial Sequence
<220> FEATURE:
<223> OTHER INFORMATION: IgGFc-binding protein peptide-1

<400> SEQUENCE: 29

Tyr Asp Leu Ala Phe Val Val Ala Ser Gln Ala Thr Lys
1               5                   10

<210> SEQ ID NO 30
<211> LENGTH: 12
<212> TYPE: PRT
<213> ORGANISM: Artificial Sequence
<220> FEATURE:
<223> OTHER INFORMATION: IgGFc-binding protein peptide-2

<400> SEQUENCE: 30

Leu Asp Ser Leu Val Ala Gln Gln Leu Gln Ser Lys
1               5                   10

<210> SEQ ID NO 31
<211> LENGTH: 14
<212> TYPE: PRT
<213> ORGANISM: Artificial Sequence
<220> FEATURE:
<223> OTHER INFORMATION: IgGFc-binding protein peptide-3

<400> SEQUENCE: 31

```
Gly Ala Thr Thr Ser Pro Gly Val Tyr Glu Leu Ser Ser Arg
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Cystatin-C peptide

<400> SEQUENCE: 32

Ala Leu Asp Phe Ala Val Gly Glu Tyr Asn Lys
1               5                   10

<210> SEQ ID NO 33
<211> LENGTH: 8
<212> TYPE: PRT
<213> ORGANISM: Artificial Sequence
<220> FEATURE:
<223> OTHER INFORMATION: Lipopolysaccharide-binding protein peptide-1

<400> SEQUENCE: 33

Ser Phe Arg Pro Phe Val Pro Arg
1               5

<210> SEQ ID NO 34
<211> LENGTH: 9
<212> TYPE: PRT
<213> ORGANISM: Artificial Sequence
<220> FEATURE:
<223> OTHER INFORMATION: Lipopolysaccharide-binding protein peptide-2

<400> SEQUENCE: 34

Ile Thr Gly Phe Leu Lys Pro Gly Lys
1               5

<210> SEQ ID NO 35
<211> LENGTH: 12
<212> TYPE: PRT
<213> ORGANISM: Artificial Sequence
<220> FEATURE:
<223> OTHER INFORMATION: Lipopolysaccharide-binding protein peptide-3

<400> SEQUENCE: 35

Val Gln Leu Tyr Asp Leu Gly Leu Gln Ile His Lys
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Alpha-1-acid glycoprotein 2 peptide-1

<400> SEQUENCE: 36

Glu His Val Ala His Leu Leu Phe Leu Arg
1               5                   10

<210> SEQ ID NO 37
<211> LENGTH: 15
<212> TYPE: PRT
<213> ORGANISM: Artificial Sequence
<220> FEATURE:
<223> OTHER INFORMATION: Alpha-1-acid glycoprotein 2 peptide-2

<400> SEQUENCE: 37
```

Asn Trp Gly Leu Ser Phe Tyr Ala Asp Lys Pro Glu Thr Thr Lys
1               5                   10                  15

```
<210> SEQ ID NO 38
<211> LENGTH: 17
<212> TYPE: PRT
<213> ORGANISM: Artificial Sequence
<220> FEATURE:
<223> OTHER INFORMATION: Alpha-1-acid glycoprotein 2 peptide-3

<400> SEQUENCE: 38
```

Glu Gln Leu Gly Glu Phe Tyr Glu Ala Leu Asp Cys Leu Cys Ile Pro
1               5                   10                  15

Arg

```
<210> SEQ ID NO 39
<211> LENGTH: 11
<212> TYPE: PRT
<213> ORGANISM: Artificial Sequence
<220> FEATURE:
<223> OTHER INFORMATION: Leucine-rich alpha-2-glycoprotein peptide-1

<400> SEQUENCE: 39
```

Ala Leu Gly His Leu Asp Leu Ser Gly Asn Arg
1               5                   10

```
<210> SEQ ID NO 40
<211> LENGTH: 10
<212> TYPE: PRT
<213> ORGANISM: Artificial Sequence
<220> FEATURE:
<223> OTHER INFORMATION: Leucine-rich alpha-2-glycoprotein peptide-2

<400> SEQUENCE: 40
```

Val Ala Ala Gly Ala Phe Gln Gly Leu Arg
1               5                   10

```
<210> SEQ ID NO 41
<211> LENGTH: 9
<212> TYPE: PRT
<213> ORGANISM: Artificial Sequence
<220> FEATURE:
<223> OTHER INFORMATION: Leucine-rich alpha-2-glycoprotein peptide-3

<400> SEQUENCE: 41
```

Gly Gln Thr Leu Leu Ala Val Ala Lys
1               5

```
<210> SEQ ID NO 42
<211> LENGTH: 7
<212> TYPE: PRT
<213> ORGANISM: Artificial Sequence
<220> FEATURE:
<223> OTHER INFORMATION: Apolipoprotein D peptide-1

<400> SEQUENCE: 42
```

Val Leu Asn Gln Glu Leu Arg
1               5

```
<210> SEQ ID NO 43
<211> LENGTH: 13
<212> TYPE: PRT
<213> ORGANISM: Artificial Sequence
<220> FEATURE:
<223> OTHER INFORMATION: Apolipoprotein D peptide-2

<400> SEQUENCE: 43
```

```
Asn Pro Asn Leu Pro Pro Glu Thr Val Asp Ser Leu Lys
1               5                   10
```

<210> SEQ ID NO 44
<211> LENGTH: 11
<212> TYPE: PRT
<213> ORGANISM: Artificial Sequence
<220> FEATURE:
<223> OTHER INFORMATION: Apolipoprotein D peptide-3

<400> SEQUENCE: 44

```
Asn Ile Leu Thr Ser Asn Asn Ile Asp Val Lys
1               5                   10
```